US007858318B2

(12) United States Patent
Stafford et al.

(10) Patent No.: US 7,858,318 B2
(45) **Date of Patent: *Dec. 28, 2010**

(54) METHODS AND COMPOSITIONS FOR VITAMIN K EPOXIDE REDUCTASE

(75) Inventors: Darrel W. Stafford, Carrboro, NC (US); Tao Li, San Diego, CA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/361,053

(22) Filed: Jan. 28, 2009

(65) Prior Publication Data

US 2009/0215061 A1 Aug. 27, 2009

Related U.S. Application Data

(63) Continuation of application No. 10/573,131, filed as application No. PCT/US2004/031481 on Sep. 23, 2004, now Pat. No. 7,687,233.

(60) Provisional application No. 60/505,527, filed on Sep. 23, 2003.

(51) Int. Cl.

| | |
|---|---|
| ***C12Q 1/68*** | (2006.01) |
| ***C12P 19/34*** | (2006.01) |
| *C07H 21/02* | (2006.01) |
| *C07H 21/04* | (2006.01) |

(52) U.S. Cl. ......................... 435/6; 435/91.2; 536/23.1; 536/24.3

(58) Field of Classification Search ....................... None
See application file for complete search history.

(56) References Cited

U.S. PATENT DOCUMENTS

| | | | | |
|---|---|---|---|---|
| 4,736,866 | A | 4/1988 | Leder et al. | |
| 4,816,397 | A | 3/1989 | Boss et al. | |
| 4,816,567 | A | 3/1989 | Cabilly et al. | |
| 5,547,835 | A | 8/1996 | Koster et al. | |
| 5,583,278 | A | 12/1996 | Alt et al. | |
| 5,625,122 | A | 4/1997 | Mak | |
| 5,686,631 | A | 11/1997 | Li et al. | |
| 5,698,765 | A | 12/1997 | Mak | |
| 5,750,825 | A | 5/1998 | Yazaki et al. | |
| 6,043,031 | A | 3/2000 | Koster et al. | |
| 6,453,244 | B1 * | 9/2002 | Oefner | 702/20 |
| 6,492,115 | B1 | 12/2002 | Guida et al. | |
| 7,445,896 | B2 | 11/2008 | Rieder et al. | |
| 2005/0164367 | A1 | 7/2005 | Fenge et al. | |
| 2005/0271644 | A1 * | 12/2005 | Oldenburg et al. | 424/94.4 |
| 2006/0084070 | A1 | 4/2006 | Rieder et al. | |
| 2006/0084081 | A1 | 4/2006 | Rieder et al. | |
| 2006/0166239 | A1 | 7/2006 | Chen et al. | |
| 2006/0194284 | A1 | 8/2006 | Scheiflinger et al. | |
| 2006/0240440 | A1 | 10/2006 | Stafford et al. | |
| 2007/0009950 | A1 | 1/2007 | Stafford et al. | |
| 2007/0190614 | A1 | 8/2007 | Stafford et al. | |
| 2007/0269866 | A1 | 11/2007 | Stafford et al. | |
| 2007/0298426 | A1 | 12/2007 | Chen et al. | |
| 2008/0050732 | A1 | 2/2008 | Rieder et al. | |
| 2008/0050733 | A1 | 2/2008 | Rieder et al. | |
| 2008/0057500 | A1 | 3/2008 | Rieder et al. | |
| 2008/0318219 | A1 | 12/2008 | Rieder et al. | |

FOREIGN PATENT DOCUMENTS

| | | | |
|---|---|---|---|
| EP | 0 127 839 | B1 | 12/1984 |
| EP | 0 154 133 | B1 | 9/1985 |
| EP | 0 368 684 | B1 | 5/1990 |
| EP | 0 549 721 | B1 | 7/1993 |
| WO | WO 88/01649 | | 3/1988 |
| WO | WO 89/12685 | A1 | 12/1989 |
| WO | WO 92/01795 | | 2/1992 |
| WO | WO 93/06213 | | 4/1993 |
| WO | WO 95/34679 | | 12/1995 |
| WO | WO 97/49802 | | 12/1997 |
| WO | WO 98/24884 | | 6/1998 |
| WO | WO 99/33983 | A1 | 7/1999 |
| WO | WO 99/43003 | | 8/1999 |
| WO | WO 00/03015 | | 1/2000 |
| WO | WO 02/40544 | A2 | 5/2002 |
| WO | WO 02/102994 | A2 | 12/2002 |
| WO | WO 2005/030039 | | 4/2005 |
| WO | WO 2005/040367 | A1 | 5/2005 |
| WO | WO 2006/044686 | | 4/2006 |
| WO | WO 2006/067116 | A1 | 6/2006 |

(Continued)

OTHER PUBLICATIONS

Kimura et al; Thrombosis research, vol. 120, pp. 181-186, 2007.*

(Continued)

*Primary Examiner*—Jehanne S Sitton
(74) *Attorney, Agent, or Firm*—Myers Bigel Sibley & Sajovec, P.A.

(57) ABSTRACT

The present invention provides a method of identifying a human subject having increased or decreased sensitivity to warfarin, comprising detecting in the subject the presence of a single nucleotide polymorphism in the VKOR gene, wherein the single nucleotide polymorphism is correlated with increased or decreased sensitivity to warfarin, thereby identifying the subject having increased or decreased sensitivity to warfarin.

15 Claims, 3 Drawing Sheets

FOREIGN PATENT DOCUMENTS

| | | |
|---|---|---|
| WO | WO 2006/089613 A1 | 8/2006 |
| WO | WO 2006/101474 | 9/2006 |

OTHER PUBLICATIONS

Rost et al; Nature vol. 427, pp. 537-541 Feb. 5, 2004.*
dbSNP rs7294, build 86, NCBI; 2000.*
Genbank Accession No: AC135050, 2002.*
Chica et al. "Semi-Rational Approaches to Engineering Enzyme Activity: Combining the Benefits of Directed Evolution and Rational Design" *Current Opinion in Biotechnology* 16:378-384 (2005).
GenBank Accession No. N63475 (2p)(Sep. 13, 2000).
GenBank Accession No. NT024812 (5p)(Jul. 4, 2003).
Hegele. "SNP Judgments and Freedom of Association" *Arterioscler Thromb. Vasc. Biol.* 22:1058-1061 (2002).
Keller and Manak. "DNA Probes" 2nd Ed., Macmillan Publishers Ltd., pp. 259 (1993).
Lucentini. "Gene Association Studies Typically Wrong" The Scientist pp. 20 (Dec. 20, 2004).
Risch. "Searching for Genetic Determinants in the New Millennium" *Nature* 405:847-856 (2000).
Sen et al. "Developments in Directed Evolution for Improving Enzyme Functions" *Appl. Biochem. Biotechnol.* 143:212-223 (2007).
European Search Report for Application EP 05733161.3, mailed Aug. 5, 2008 (4 pages).
European Search Report for Application EP 04789039.7, mailed Oct. 7, 2008 (6 pages).
Database Accession No. ADA57411 "Human Secreted Protein #230", Nov. 20, 2003 (first entry)(reissued Jun. 15, 2007).
Fair et al. "Biosynthesis and Secretion of Factor VII, Protein C, Protein S, and the Protein C Inhibitor from a Human Hepatoma Cell Line" *Blood* 67:64-70 (1986).
Ferland. "The Vitamin-K Dependent Proteins: An Update" *Nutrition Reviews* 56(8):223-230 (1998).
Furie et al. "Molecular Basis of Vitamin K-Dependent y-Carboxylation" *The Journal of the American Society of Hematology* 75:1753-1762 (1990).
Gainnelli et al. "Hemophilia B: Database of Point Mutations and Short Additions and Deletions—Eighth Edition" *Nucleic Acids Research* 26(1):265-268 (1998).
Kulman et al. "Primary Structure and Tissue Distribution of Two Novel Proline-Rich γ-Carboxyglutamic Acid Proteins" *Proc. Natl. Acad, Sci.* USA 94:9058-9062 (1997).
McVey et al. "Factor VII Deficiency and the FVII Mutation Database" *Human Mutation* 17:3-17 (2001).
Munns et al. "Vitamin K-Dependent Synthesis and Modification of Precursor Prothrombin in Cultured H-35 Hepatoma Cells" *Proc. Natl. Acad. Sci. USA* 73:2803-2807 (1976).
Price et al. "Matrix Gla Protein, a New γ-Carboxyglutamic Acid-Containing Protein Which is Associated with the Organic Matrix of Bone" *Biochemical and Biophysical Research Communications* 117(3):765-771 (1983).
Suttie. "Synthesis of Vitamin K-Dependent Proteins' *FASEB J.* 7:445-452 (1993).
Tsaioun. "Vitamin K-Dependent Proteins in the Developing and Aging Nervous System" *Nutrition Reviews* 57(8):231-240 (1999).
European Search Report for Application EP 070109353 mailed, Aug. 30, 2007.
Hanumanthaiah et al. "Developmental Expression of Vitamin K-Dependent Gamma-Carboxylase Activity in Zebrafish Embryos: Effect of Warfarin" *Blood Cells, Molecules, and Diseases* 27(6):992-999 (2001).
Clark et al. "The Secreted Protein Discovery Initiative (SPDI), a large scale effort to identify novel human secreted and transmembrane proteins: a bioinformatic assessment" *Genome Res.* 13:2265-2270 (2003).
Specification of U.S. Appl. No. 11/787,072, filed Apr. 13, 2007, entitled "Methods and Compositions for Producing Vitamin K Dependent Proteins".
Specification of U.S. Appl. No. 11/643,563, filed Dec. 21, 2006, entitled "Method of Producing Biologically Active Vitamin K Dependent Proteins by Recombinant Methods".
GenBank Accession No. BC000828, *Homo sapiens* vitamin K epoxide reductase complex, CDNA clone IMAGE:3455200, Aug. 11, 2006.
GenBank Accession No. BC000828, *Homo sapiens* vitamin K epoxide reductase complex, CDNA clone IMAGE:3455200, Sep. 1, 2006.
GenBank Accession No. BC002911, *Homo sapiens* vitamin K epoxide reductase complex, clone MGC:11276, Jul. 15, 2006.
GenBank Accession No. BC002911, *Homo sapiens*, clone MGC:11276, Jul. 12, 2001.
GenBank Accession No. BC027734, *Homo sapiens* vitamin K epoxide reductase complex, clone MGC:29720, Jul. 15, 2006.
GenBank Accession No. NG_005631, *Homo sapiens* vitamin K epoxide reductase complex, LOC441241, Aug. 5, 2006.
GenBank Accession No. NM_178600, *Mus musculus* vitamin K epoxide reductase complex, Vkorc1, Aug. 6, 2006.
GenBank Accession No. NM024006.1, *Homo sapiens* hypothetical protein, Image 3455200, Oct. 5, 2003.
GenBank Accession No. NM024006, *Homo sapiens* vitamin K epoxide reductase complex, VKORC1, Aug. 13, 2006.
GenBank Accession No. NM203335, *Rattus norvegicus* vitamin K epoxide reductase complex, Vkorc1, Jan. 15, 2006.
GenBank Accession No. NM206807.1, *Gallus gallus* vitamin K epoxide reductase complex, VKORC1, Jun. 25, 2006.
GenBank Accession No. NM206824.1, *Homo sapiens* vitamin K epoxide reductase complex, VKORC1, Aug. 13, 2006.
ICOS "Factor IX Cell Culture Process" Version 2.0 (12 pages) (2006).
Bogousslaysky et al. "Anticoagulant-induced intracerebral bleeding in brain ischemia" *Acta Neurol Scand.* 77:464-471 (1985).
Chen et al. "Calcium Phosphate-Mediated Gene Transfer: A Highly Efficient Transfection System for Stably Transforming Cells with Plasmid DNA" *BioTechniques* 6(7):632-638 (1988).
Ekelund et al. "Combined Deficiency of Coagulation Factors II, VII, IX, and X: A Case of Probable Congenital Origin" *Pediatric Hematology and Oncology* 3:187-193 (1986).
Furuya et al. "Genetic polymorphism of CYP2C9 and its effect on warfarin maintenance dose requirement in patients undergoing anticoagulation therapy" *Pharmacogenetics* 5:389-392 (1995).
Gan et al. "Racial Background Is a Determinant Factor in the Maintenance Dosage of Warfarin" *International Journal of Hematology* 78:84-86 (2003).
Gullov et al. "Bleeding Complications to Long-Term Oral Anticoagulant Therapy" *Journal of Thrombosis and Thrombolysis* 1:17-25 (1994).
Nasu et al. "Genetic analysis of *CYP2C9* polymorphism in a Japanese population" *Pharmacogenetics* 7:405-409 (1997).
Prentice "Acquired Coagulation Disorders" *Clin. Haematol.* 14(2):413-442 (1985).
Suttie "The Biochemical Basis of Warfarin Therapy" *Adv. Exp. Med. Bio.* 214:3-16 (1987).
Vermeer et al. "Vitamin K-Dependent Carboxylase" *Haematologia* 18(2):71-97 (1985).
Vincente et al. "Congenital Deficiency of Vitamin K-Dependent Coagulation Factors and Protein C" *Thromb Haemostas* (*Stuttgart*) 51(3):343-346 (1984).
Wallace et al. "A major gene controlling warfarin-resistance in the house mouse" *J. Hyg., Camb.* 76:173-181 (1976).
Yu et al. "Factors determining the maintenance dose of warfarin in Chinese patients" *Q J Med* 89:127-135 (1996).
Zwaal et al. "Lipid-protein interactions in blood coagulation" *Biochimica et Biophysica Acta* 1376:433-453 (1998).
Aithal et al. "Association of polymorphisms in the cytochrome P450 CYP2C9 with warfarin dose requirement and risk of bleeding complications" *The Lancet* 353(9154):717-719 (1999).
Cheung et al. "Localization of a Metal-Dependent Epitope to the Amino Terminal Residues 33-40 of Human Factor IX" *Thrombosis Research* 80(2):419-427 (1995).

Davis et al. "A quantum chemical study of the mechanism of action of Vitamin K carboxylase (VKC) III. Intermediates and transition states" *Journal of Molecular Graphics and Modelling* (Nov. 6, 2006), [Epub ahead of print].
Davis et al. "A quantum chemical study of the mechanism of action of Vitamin K epoxide reductase (VKOR) II. Transition states" *Journal of Molecular Graphics and Modelling* (Nov. 6, 2006), [Epub ahead of print].
Herlitschka et al. "Overexpression of Human Prothrombin in Permanent Cell Lines Using a Dominant Selection/Amplification Fusion Marker" *Protein Expression and Purification* 8:358-364 (1996).
Oldenburg et al. "Vitamin K Epoxide Reductase Complex Subunit 1 (VKORC1): The Key Protein of the Vitamin K Cycle" *Antioxidants & Redox Signaling* 8(3 & 4):347-353 (2006).
Rettie et al. "A common genetic basis for idiosyncratic toxicity of warfarin and phenytoin" *Epilepsy Research* 35: 253-255 (1999).
Schmidt-Krey et al. "Two-dimensional crystallization of human vitamin K-dependent γ-glutamyl carboxylase" *Journal of Structural Biology* 157:437-442 (2007).
Takahashi et al. "Population differences in S-warfarin metabolism between *CYP2C9* genotype-matched Caucasian and Japanese patients" *Clinical Pharmacology & Therapeutics* 73(3):253-263 (2003).
Wallin et al. "Warfarin and the Vitamin K-Dependent γ-Carboxylation System" *TRENDS in Molecular Medicine* 10(7):299-302 (2004).
Wallin et al. "Vitamin K 2,3-epoxide reductase and the vitamin K-dependent γ-carboxylation system" *Thrombosis Research* 108:221-226 (2003).
Wu et al. "Cloning and expression of the cDNA for human gamma-glutamyl carboxylase" *Science* 254(5038):1634-1636 (1991).
Xie et al, "*CYP2C9* allelic variants: ethnic distribution and functional significance" *Advanced Drug Delivery Reviews* 54: 1257-1270 (2002).
Absher et al. "Patient-Specific Factors Predictive of Warfarin Dosage Requirements" *Ann Pharmacother* 36(10):1512-1517 (2002).
Chenhsu et al. "Long-Term Treatment with Warfarin in Chinese Population" *Ann Pharmacother* 34(12):1395-1401 (2000).
Devlin et al. "A Comparison of Linkage Disequilibrium Measures for Fine-Scale Mapping" *Genomics* 29(2):311-322 (1995).
Durrin et al. "Vitamin D receptor 3'-untranslated region polymorphisms: lack of effect on mRNA stability" *Biochimica et Biophysica Acta* 1453(3):311-320 (1999).
Fang et al. "National Trends in Antiarrhythmic and Antithrombotic Medication Use in Atrial Fibrillation" *Arch Intern Med* 164(1):55-60 (2004).
Himly et al. "Defective Vaccinia Virus as a Biologically Safe Tool for the Overproduction of Recombinant Human Secretory Proteins" *Protein Expression and Purification* 14(3):317-326 (1998).
Hirsh et al. "Antithrombotic therapy in deep vein thrombosis and pulmonary embolism" *American Heart Journal* 123(4, Pt. 2):1115-1122 (1992).
Jones et al. "A Cellular DNA-Binding Protein That Activates Eukaryotic Transcription and DNA Replication" *Cell* 48(1):79-89 (1987).
Kirchheiner et al. "Clinical consequences of cytochrome P450 2C9 polymorphisms" *Clinical Pharmacology & Therapeutics* 77(1):1-16 (2005).
Landefeld et al. "Anticoagulant-Related Bleeding: Clinical Epidemiology, Prediction, and Prevention" *The American Journal of Medicine* 95(3):315-328 (1993).
Loebstein et al. "Interindividual variability in sensitivity to warfarin—Nature or nurture?" *Clinical Pharmacology & Therapeutics* 70(2):159-164 (2001).
Mountford et al. "Internal ribosome entry sites and dicistronic RNAs in mammalian transgenesis" *Trends Genet.* 11(5):179-184 (1995).
Pechlaner et al. "A New Case of Combined Deficiency of Vitamin K Dependent Coagulation Factors" *Thrombosis and Haemostasis* 68(5):617 (1992).
Pennisi, Elizabeth "A Closer Look at SNPs Suggests Difficulties" *Science* 281(5834):1787-1789 (1998).
Stanley et al. "Identification of a vitamin K-dependent carboxylase in the venom duct of a *Conus* snail" *FEBS Letters* 407(1):85-88 (1997).
Suttie et al. "Mechanisms of action of vitamin K: synthesis of gamma-carboxyglutamic acid" *CRC Crit Rev. Biochem* 8(2):191-223 (1980).
Wallin et al. "Purification of Warfarin-Sensitive Vitamin K Epoxide Reductase" *Methods in Enzymology* 282:395-408 (1997).
Wu et al. "Characterization of the γ-Glutamyl Carboxylase" *Thrombosis and Haemostasis* 78(1):599-604 (1997).
Altschul et al. "Gapped BLAST and PSI-BLAST: a new generation of protein database search programs" *Nucleic Acids Research* 25(17):3389-3402 (1997).
Bandyopadhyay et al. "γ-Glutamyl carboxylation: An extracellular posttranslational modification that antedates the divergence of □ollusks, arthropods, and chordates" *PNAS* 99(3):1264-1269 (2002).
Bell et al. "Warfarin and the inhibition of vitamin K activity by an oxide metabolite" *Nature* 237:32-33 (1972).
Berkner et al. "The Vitamin K-Dependent Carboxylase" *J. Nutr.* 130:1877-1880 (2000).
Blann et al. "Racial background is a determinant of average warfarin dose required to maintain the INR between 2.0 and 3.0" *Br J Haematol.* 107(1):207-209 (1999).
Boneh et al. "Hereditary Deficiency of Vitamin K-Dependent Coagulation Factors With Skeletal Abnormalities" *American Journal of Medical Genetics* 65:241-243 (1996).
Brenner et al. "A Missense Mutation in γ-Glutamyl Carboxylase Gene Causes Combined Deficiency of All Vitamin K-Dependent Blood Coagulation Factors" *Blood* 92(12):4554-4559 (1998).
Cain et al. "Assembly of the Warfarin-sensitive Vitamin K 2,3-Epoxide Reductase Enzyme Complex in the Endoplasmic Reticulum Membrane" *The Journal of Biological Chemistry* 272(46):29068-29075 (1997).
Cain et al. "Warfarin Resistance Is Associated with a Protein Component of the Vitamin K 2,3-Epoxide Reductase Enzyme Complex in Rat Liver" *Thromb Haemost* 80:128-33 (1998).
Camire et al. "Enhanced γ-Carboxylation of Recombinant Factor X Using a Chimeric Construct Containing the Prothrombin Propeptide" *Biochemistry* 39:14322-14329 (2000).
Carter et al. "Prothrombin G20210A is a bifunctional gene polymorphism" *Thromb Haemost.* 87(5):846-853(2002).
Chu et al. "A Mutation in the Propeptide of Factor IX Leads to Warfarin Sensitivity by a Novel Mechanism" *J. Clin. Invest.* 98(7):1619-1625 (1996).
Chu et al. "Purified vitamin K epoxide reductase alone is sufficient for conversion of vitamin K epoxide to vitamin K and vitamin K to vitamin $KH_2$" *PNAS* 103(51):19308-19313 (2006).
International Search Report for PCT/EP2006/000734, dated May 11, 2006.
Crawford et al. "Haplotype Diversity across 100 Candidate Genes for Inflammation, Lipid Metabolism, and Blood Pressure Regulation in Two Populations" *Am J. Hum. Genet.* 74:610-622 (2004).
Derian et al. "Inhibitors of 2-Ketoglutarate-dependent Dioxygenases Block Aspartyl β-Hydroxylation of Recombinant Human Factor IX in Several Mammalian Expression Systems" *The Journal of Biological Chemistry* 264(12):6615-6618 (1989).
Dockal et al. "Five recombinant fragments of human serum albumin-tools for the characterization of the warfarin binding site" *Protein Sci.* 9:1455-1465 (2000).
Dockal et al. "The Three Recombinant Domains of Human Serum Albumin" *The Journal of Biological Chemistry* 274(41):29303-29310 (1999).
Drysdale et al. "Complex promoter and coding region β2-adrenergic receptor haplotypes alter receptor expression and predict in vivo responsiveness" *PNAS* 97(19):10483-10488 (2000).
Esmon et al. "The Functional Significance of Vitamin K Action" *The Journal of Biological Chemistry* 250(11):4095-4099 (1975).
Esmon et al. "The New Carboxylation Reaction" *The Journal of Biological Chemistry* 250(12):4744-4748 (1975).
Fasco et al. "Formation of Hydroxyvitamin K by Vitamin K Epoxide Reductase of Warfarin-resistant Rats" *The Journal of Biological Chemistry* 258(7):4372-4380 (1983).
Fasco et al. "Warfarin Inhibition of Vitamin K 2,3-Epoxide Reductase in Rat Liver Microsomes" *Biochemistry* 22:5655-5660 (1983).

Furie et al. "The Molecular Basis of Blood Coagulation" *Cell* 53:505-518 (1988).

Furie et al. "Vitamin K-Dependent Biosynthesis of γ-Carboxyglutamic Acid" *Blood* 93(6):1798-1808 (1999).

Gage et al. "Adverse Outcomes and Predictors of Underuse of Antithrombic Therapy in Medicare Beneficiaries with Chronic Atrial Fibrillation" *Stroke* 31:822-827 (2000).

Gage et al. "Use of pharmacogenetics and clinical factors to predict the maintenance dose of warfarin" *Thromb Haemost*. 91(1):87-94 (2004).

GenBank Accession No. AC135050, *Homo sapiens* chromosome 16 clone RP11-196G11, complete sequence, Oct. 5, 2002.

GenBank Accession No. AK002742, *Mus musculus* adult male kidney cDNA, clone:0610033K05, Jul. 10, 2000.

GenBank Accession No. AK013996, *Mus musculus* 13 days embryo head cDNA, clone:3110005B16, Jul. 10, 2000.

GenBank Accession No. AV003686, *Mus musculus* C57BL/8J kidney *Mus musculus* cDNA, clone:0610033K05, Unpublished 1999.

GenBank Accession No. AV162712, *Mus musculus* head C57BL/6 13-dat embryo *Mus Musculus* cDNA, clone:3110005B16, Unpublished 1999.

GenBank Accession No. AY587020, *Homo sapiens* vitamin K epoxide reductase complex, Mar. 31, 2004.

GenBank Accession No. BC000828, *Homo sapiens* vitamin K epoxide reductase complex, CDNA clone Image:3455200, Nov. 15, 2000.

GenBank Accession No. BC002911.1, *Homo sapiens*, clone MGC:11276, Feb. 5, 2001.

GenBank Accession No. BC002911.2, *Homo sapiens* vitamin K epoxide reductase complex, clone MGC:11276, Feb. 5, 2001.

GenBank Accession No. BCO27734, *Homo sapiens* vitamin K-epoxide reductase complex, clone MGC:29720, Apr. 8, 2002.

GenBank Accession No. BY703248, adult male kidney *Mus musculus*, clone 0610033K05, Dec. 16, 2002.

GenBank Accession No. NG_005631, *Homo sapiens* vitamin K epoxide reductase complex, LOC441241, derived from AC073210.8, *Homo sapiens* BAC clone RP11-460N20, complete sequence, Jun. 10, 2000.

GenBank Accession No. NM_178600, *Mus musculus* vitamin K epoxide reductase complex, Vkorc1, derived from AK003237.1, *Mus musculus* 18-day embryo whole body cDNA, clone:1110001K05, Jul. 10, 2000 and CD774813.1, NIH_BMAP_MHI *Mus musculus* cDNA clone, Jul. 2, 2003.

GenBank Accession No. NM_178600.2, *Mus musculus* vitamin K epoxide reductase complex, Vkorc1, Mar. 16, 2004.

GenBank Accession No. NM_024006.1, *Homo sapiens* hypothetical protein, Image 3455200, Oct. 5, 2003.

GenBank Accession No. NM_024006.4, *Homo sapiens* vitamin K epoxide reductase complex, VKORC1, Mar. 11, 2007.

GenBank Accession No. NM_203335, *Rattus norvegicus* vitamin K epoxide reductase complex, Vkorc1, derived from CB314647.1, NICHD_Rr_Pit1 *Rattus norvegicus* cDNA clone, Image:6890244, Mar. 3, 2003, AY423047.1, *Rattus norvegicus* vitamin K epoxide reductase complex subunit 1(Vkorc1) mRNA, complete cds, Sep. 25, 2003 and AW253787.1, UI-R-BJ0-acz-d-05-0-UI.s1 UI-R-BJ0 *Rattus norvegicus* cDNA clone, Dec. 17, 1999.

GenBank Accession No. NM_206807, *Gallus gallus* vitamin K epoxide reductase complex, VKORC1, derived from AW355622, *Gallus gallus* cDNA clone pftlc.pk003.d10, Jun. 23, 2006, and BU114821.1, CHSEQCHL14 *Gallus gallus* cDNA clone ChEST105p15, Nov. 25, 2002.

GenBank Accession No. NM_206824, *Homo sapiens* vitamin K epoxide reductase complex, VKORC1, derived from BI822140.1, 603039843F1 NIH_MGC_115 *Homo sapiens* cDNA clone Image:5180554, Oct. 4, 2001, AK129513.1, *Homo sapiens* cDNA FLJ26002 fis, clone DMC07743, Jul. 31, 2003 and CD249837.1, NIH_MGC_172 *Homo sapiens* cDNA, Unpublished 1999.

GenBank Accession No. NP_848715, vitamin K epoxide reductase complex, subunit 1 [Mus musculus], derived from AK003237.1, *Mus musculus* 18-day embryo whole body cDNA, clone:1110001K05, Jul. 10, 2000 and CD774813.1, NIH_BMAP_MHI *Mus musculus* cDNA clone, Jul. 2, 2003.

Swiss-Prot Accession No. Q9CRC0, Vitamin K epoxide reductase complex subunit 1 (Vitamin K1 2,3-epoxide reductase subunit 1), Jun. 1, 2001.

Goldsmith et al. "Studies on a Family with Combined Functional Deficiencies of Vitamin K-dependent Coagulation Factors" *J. Clin. Invest*. 69:1253-1260 (1982).

Gossen et al. "Inducible gene expression systems for higher eukaryotic cells" *Current Opinion in Biotechnology* 5:516-520 (1994).

Greaves et al. "Heritable Resistance to Warfarin in Rats" *Nature* 215:877-878 (1967).

Guenthner et al. "Co-purification of Microsomal Epoxide Hydrolase with the Warfarin-Sensitive Vitamin—K1 Oxide Reductase of the Vitamin K Cycle" *Biochemical Pharmacology* 55:169-175 (1998).

Hacker et al. "Lack of association between an interleukin-1 receptor antagonist gene polymorphism and ulcerative colitis" *Gut* 40:623-627 (1997).

Hallgren et al. "Carboxylase overexpression effects full carboxylation but poor release and secretion of factor IX: implications for the release of vitamin K-dependent proteins" *Biochemistry* 41(50):15045-55 (2002).

Higashi et al. "Association between CYP2C9 genetic variants and anticoagulation-related outcomes during warfarin therapy" *JAMA* 287(13):1690-1698 (2002).

Hirsh et al. "Oral Anticoagulants: Mechanism of Action, Clinical Effectiveness, and Optimal Therapeutic Range" *Chest* 119:8s-21s (2001).

Houben et al. "Osteocalcin binds tightly to the γ-glutamylcarboxylase at a site distinct from that of the other known vitamin K-dependent proteins" *Biochem. J*. 341:265-269 (1999).

Huisse et al. "Mechanism of the Abnormal Vitamin K-dependent γ-Carboxylation Process in Human Hepatocellular Carcinomas" *Cancer* 74:1533-41 (1994).

Jackson et al. "Identification of a consensus motif for retention of transmembrane proteins in the endoplasmic reticulum" *The EMBO Journal* 9(10):3153-3162 (1990).

Johnson et al. "Characterization of a Variant Prothrombin in a Patient Congenitally Deficient in Factors II, VII, IX, and X" *British Journal of Haematology* 44:461-469 (1980).

Kaminsky et al. "Correlation of human cytochrome P4502C substrate specificities with primary structure: warfarin as a probe" *Mol Pharmacol*. 43(2):234-239 (1993).

Kaminsky et al. "Human hepatic cytochrome P-450 composition as probed by in vitro microsomal metabolism of warfarin" *Drug Metab Dispos*. 12(4):470-477 (1984).

Kaufman et al. "Expression, Purification, and Characterization of Recombinant γ-Carboxylated Factor IX Synthesized in Chinese Hamster Ovary Cells" *The Journal of Biological Chemistry* 261(21):9622-9628 (1986).

Kohn et al. "Genomic assignment of the warfarin resistance locus, *Rw*, in the rat" *Mammalian Genome* 10:696-698 (1999).

Kozak et al. "An analysis of 5'-noncoding sequences from 699 vertebrate messenger RNAs" *Nucleic Acids Research* 15(20):8125-8148 (1987).

Laupacis et al. "Antithrombotic therapy in atrial fibrillation" *Chest* 114:579s-589s (1998).

Lee et al. "Glucocorticoids regulate expression of dihydrofolate reductase cDNA in mouse mammary tumour virus chimaeric plasmids" *Nature* 294:228-232 (1981).

Lesko et al. "Translation of pharmacogenomics and pharmacogenetics: a regulatory perspective" *Nat Rev Drug Discov*. 3(9):763-769 (2004).

Li et al. "Indentification of a *Drosophila* Vitamin K-dependent γ-Glutamyl Carboxylase" *The Journal of Biological Chemistry* 275:18291-18296 (2000).

Lin et al. "Binding of the Factor IX γ-Carboxyglutamic Acid Domain to the Vitamin K-dependent γ-Glutamyl Carboxylase Active Site Induces an Allosteric Effect That May Ensure Processive Carboxylation and Regulate the Release of Carboxylated Product" *The Journal of Biological Chemistry* 279(8):6560-6566 (2004).

Lin et al. "The Putative Vitamin K-dependent γ-Glutamyl Carboxylase Internal Propeptide Appears to Be the Propeptide Binding Site" *The Journal of Biological Chemistry* 277(32):28584-28591 (2002).

Malhotra et al. "The Kinetics of Activation of Normal and γ-Carboxyglutamic Acid-deficient Prothrombins" *The Journal of Biological Chemistry* 260(1):279-287 (1985).

Manfioletti et al. "The Protein Encoded by a Growth Arrest-Specific Gene (*gas6*) Is a New Member of the Vitamin K-Dependent Proteins Related to Protein S, a Negative Coregulator in the Blood Coagulation Cascade" *Molecular and Cellular Biology* 13(8):4976-4985 (1993).

Mann et al. "Cofactor proteins in the assembly and expression of blood clotting enzyme complexes" *Annu Rev Biochem*. 57:915-56 (1988).

Martin et al. "Warfarin-resistance genotype determination in the Norway rat, *Rattus norvegicus" Laboratory Animals* 13:209-214 (1979).

Massari et al. "Helix-Loop-Helix Proteins: Regulators of Transcription in Eucaryotic Organisms" *Molecular and Cellular Biology* 20(2):429-440 (2000).

McGraw et al. "Evidence for a prevalent dimorphism in the activation peptide of human coagulation factor IX" *Proc. Natl. Acad. Sci. USA* 82:2847-2851 (1985).

McManus et al. "Gene Silencing in Mammals by Small Interfering RNAs" *Nature Reviews* 3:737-747 (2002).

McMillan et al. "Congenital Combined Deficiency of Coagulation Factors II, VII, IX, and X" *Medical Intelligence* 274(23)1313-1315 (1966).

Moor et al. "Coagulation Factor VII Mass and Activity in Young Men With Myocardial Infarction at a Young Age" *Arteriosclerosis, Thrombosis, and Vascular Biology* 15:655-664 (1995).

Morris et al. "Processive Post-translational Modification" *The Journal of Biological Chemistry* 270(51):30491-30498 (1995).

Morris et al. "Characterization of the Purified Vitamin K-dependent γ-Glutamyl Carboxylase" *The Journal of Biological Chemistry* 268(12):8735-8742 (1993).

Morrissey et al. "Quantitation of Activated Factor VII Levels in Plasma Using a Tissue Factor Mutant Selectively Deficient in Promoting Factor VII Activation" *Blood* 81(3):734-744 (1993).

Mumberg et al. "Regulatable promoters of *Saccharomyces cerevisiae*: comparison of transcriptional activity and their use for heterologous expression" *Nucleic Acids Research* 22(25):5767-5768 (1994).

Mukharji et al. "Purification of a vitamin K epoxide reductase that catalyzes conversion of vitamin K 2,3-epoxide to 3-hydroxy-2-methyl-3-phytyl-2,3-dihydronaphthoquinone" *Proc. Natl. Acad. Sci. USA*—82:2713-2717 (1985).

Mutero et al. "Resistance-associated point mutations in insecticide-insensitive acetylcholinesterase" *Proc. Natl. Acad. Sci.* 91:5922-5926 (1994).

Mutucumarana et al. "A Conserved Region of Human Vitamin K-dependent Carboxylase Residues 393 and 404 is Important for Its Interaction with the Glutamate Substrate" *The Journal of Biological Chemistry* 278:46488-46493 (2003).

Mutucumarana et al. "Expression and Characterization of the Naturally Occurring Mutation L394R in Human γ-Glutamyl Carboxylase" *The Journal of Biological Chemistry* 275(42):32572-32577 (2000).

Nellen et al. "What makes an mRNA anti-sense-itive" *TIBS* 18:419-423 (1993).

Nelsestuen et al. "Role of γ-Carboxyglutamic Acid" *The Journal of Biological Chemistry* 251(22):6886-6893 (1976).

Nelsestuen et al. "The Mode of Action of Vitamin K" *The Journal of Biological Chemistry* 249(19):6347-6350 (1974).

Oldenburg et al. "Congenital Deficiency of Vitamin K Dependent Coagulation Factors in Two Families Presents as a Genetic Defect of the Vitamin K-Epoxide-Reductase-Complex" *Thromb Haemost* 84:937-941 (2000).

O'Reilly et al. "Hereditary Transmission of Exceptional Resistance to Coumarin Anticoagulant Drugs" *The New England Journal of Medicine* 271:809-815 (1964).

O'Reilly et al. "The Second Reported Kindred With Hereditary Resistance to Oral Anticoagulant Drugs" *The New England Journal of Medicine* 282:1448-1451 (1970).

Pauli et al. "Association of Congenital Deficiency of Multiple Vitamin K-dependent Coagulation Factors and the Phenotype of the Warfarin Embryopathy: Clues to the Mechanism of Teratogenicity of Coumarin Derivatives" *Am. J. Hum. Genet*. 41:566-583 (1987).

Petersen et al. "Probing the Structure of the Warfarin-Binding Site on Human Serum Albumin Using Site-Directed Mutagenesis" *Proteins* 47:116-125 (2002).

Presnell et al. "The Vitamin K-dependent Carboxylase" *Thromb Haemost* 87:937-946 (2002).

Presnell et al. "A Novel Fluorescence Assay To Study Propeptide Interaction with γ-Glutamyl Carboxylase" *Biochemistry* 40:11723-11733 (2001).

Price "Role of Vitamin-K-Dependent Proteins in Bone Metabolism" *Ann Rev Nutr* 8:565-583 (1988).

Rehemtulla et al. "In vitro and in vivo functional characterization of bovine vitamin K-dependent γ-carboxylase expressed in Chinese hamster ovary cells" *Proc. Natl. Acad. Sci*. USA 90:4611-4615 (1993).

Rettie et al. "Hydroxylation of warfarin by human cDNA-expressed cytochrome P-450: a role for P-4502C9 in the etiology of (S)-warfarin-drug interactions" *Chem Res Toxicol*. 5(1):54-59 (1992).

Rusconi et al. "RNA aptamers as reversible antagonists of coagulation factor IXa" *Nature* 419:90-94 (2002).

Russell et al. "Nucleotide Sequence of the Yeast Alcohol Dehydrogenase II Gene" *The Journal of Biological Chemistry* 258(4):2674-2682 (1983).

Scahill et al. "Expression and characterization of the product of a human immune interferon cDNA gene in Chinese hamster ovary cells" *Proc. Natl. Acad. Sci*. USA 80:4654-4658 (1993).

Seffernick et al. "Melamine Deaminase and Atrazine Chlorohydrolase: 98 Percent Identical but Functionally Different" *Journal of Bacteriology* 183(8):2405-2410 (2001).

Soute et al. "Characteristics of recombinant W501S mutated human γ-glutamyl carboxylase" *Journal of Thrombosis and Haemostasis* 2:597-604 (2004).

Sperling et al. "Metal Binding Properties of γ-Carboxyglutamic Acid" *The Journal of Biological Chemistry* 253(11):3898-3906 (1978).

Spronk et al. "Novel mutation in the γ-glutamyl carboxylase gene resulting in congenital combined deficiency of all vitamin K-dependent blood coagulation factors" *Blood* 96(10):3650-3652 (2000).

Single Nucleotide Polymorphism (SNP) RefSNP(rs#) rs9923231; GenBank Accession No. NT_024812.10, Nov. 5, 2003.

Single Nucleotide Polymorphism (SNP) RefSNP(rs#) rs9934438; GenBank Accession No. NC_000016.5, Aug. 10, 2004.

Single Nucleotide Polymorphism (SNP) RefSNP(rs#) rs9934438; GenBank Accession No. NT_024812.10, Mar. 19, 2004, Details: ss21323934.

Single Nucleotide Polymorphism (SNP) RefSNP(rs#) rs9934438; GenBank Accession No. NT_024812.10, Nov. 5, 2003, Details: ss13773513.

Single Nucleotide Polymorphism (SNP) RefSNP(rs#) rs9934438; GenBank Accession No. NT_024812.10, Feb. 20, 2004, Details: ss19348150.

Single Nucleotide Polymorphism (SNP) RefSNP(rs#) rs8050394; GenBank Accession No. NT_010393, Jul. 4, 2003.

Single Nucleotide Polymorphism (SNP) RefSNP (rs#) rs8359612; GenBank Accession No. AACN010884940, Sep. 14, 2003.

Single Nucleotide Polymorphism (SNP) RefSNP (rs#) rs7294; GenBank Accession No. AA708782, Aug. 23, 1999.

Stafford et al. "The vitamin K cycle" *Journal of Thrombosis and Haemostasis* 3:1873-1878 (2005).

Stanley et al. "Amino Acids Responsible for Reduced Affinities of Vitamin K-Dependent Propeptides for the Carboxylase" *Biochemistry* 38:15681-15687 (1999).

Stanley et al. "Role of the Propeptide and γ-Glutamic Acid Domain of Factor IX for in Vitro *Carboxylation by the Vitamin K-Dependent Carboxylase" Biochemistry* 37:13262-13268 (1998).

Stanley et al. "The Propeptides of the Vitamin K-dependent Proteins Possess Different Affinities for the Vitamin K-dependent Carboxylase" *The Journal of Biological Chemistry* 274:16940-16944 (1999).
Stein et al. "Antithrombotic therapy in patients with mechanical and biological prosthetic heart valves" *Chest* 108:371S-379S (1995).
Stenflo et al. "Vitamin K-dependent formation of gamma-carboxyglutamic acid" *Annu Rev Biochem*. 46:157-72 (1977).
Stitt et al. "The Anticoagulation Factor Protein S and Its Relative, Gas6, Are Ligands for the Tyro 3/Axl Family of Receptor Tyrosine Kinases" *Cell* 80:661-670 (1995).
Strausberg et al. "Generation and initial analysis of more than 15,000 full-length human and mouse cDNA sequences" *PNAS* 99(26):16899-16903 (2002).
Sun et al. "Vitamin K epoxide reductase significantly improves carboxylation in a cell line overexpressing factor X" *Blood* 106(12):3811-3815 (2005).
Terai et al. "Human homologue of maid: A dominantly inhibitory helix-loop-helix protein associated with liver-specific gene expression" *Hepatology* 32(2):357-66 (2000).
Tie et al. "Determination of Disulfide Bond Assignment of Human Vitamin K-dependent γ-Glutamyl Carboxylase by Matrix-assisted Laser Desorption/Ionization Time-of-Flight Mass Spectrometry" *The Journal of Biological Chemistry* 278:45468-45475 (2003).
Tie et al. "A topological study of the human γ-glutamyl carboxylase" *Blood* 96:973-978 (2000).
Tie et al. "Identification of the N-Linked Glycosylation Sites of Vitamin K-Dependent Carboxylase and Effect of Glycosylation on Carboxylase Function" *Biochemistry* 45:14755-14763 (2006).
Tie et al. "Chemical Modification of Cysteine Residues Is a Misleading Indicator of Their Status as Active Site Residues in the Vitamin K-dependent γ-Glutamyl Carboxylation" *The Journal of Biological Chemistry* 279:54079-54087 (2004).
Tie et al. "Membrane Topology Mapping of Vitamin K Epoxide Reductase by in Vitro Translation/Cotranslocation" *The Journal of Biological Chemistry* 280:16410-16416 (2005).
Toomajian et al. "Sequence Variation and Haplotype Structure at the Human HFE Locus" *Genetics* 161:1609-1623 (2002).
Uhlmann et al. "Antisense Oligonucleotides: A New Therapeutic Principle" *Chemical Reviews* 90(4):543-584 (1990).
Wajih et al. "Engineering of a Recombinant Vitamin K-dependent γ-Carboxylation System with Enhanced γ-Carboxyglutamic Acid Forming Capacity" *The Journal of Biological Chemistry* 280(11):10540-10547 (2005).
Wajih et al. "The Inhibitory Effect of Calumenin on the Vitamin K-dependent γ-Carboxylation System" *The Journal of Biological Chemistry* 279(24):25276-25283 (2004).
Wajih et al. "Increased Production of Functional Recombinant Human Clotting Factor IX by Baby Hamster Kidney Cells Engineered to Overexpress VKORC1, the Vitamin K 2,3-Epoxide-reducing Enzyme of the Vitamin K Cycle" *The Journal of Biological Chemistry* 280(36):31603-31607 (2005).
Wallace et al. "Hybridization of synthetic oligodeoxyribonucleotides to Φx174 DNA: the effect of single base pair mismatch" *Nucleic Acids Research* 6(11):3543-3557 (1979).
Wallin et al. "A molecular mechanism for genetic warfarin resistance in the rat" *The FASEB Journal* 15:2542-2544 (2001).
Wallin et al. "Vitamin K-dependent Carboxylation and Vitamin K Metabolism in Liver" *J. Clin. Invest*. 76:1879-1884 (1985).
Wang et al. "Identification of a gene encoding a typical γ-carboxyglutamic acid domain in the tunicate *Halocynthia roretzi*" *Journal of Thrombosis and Haemostasis* 1:118-123 (2003).
Ware et al. "Factor IX San Dimas" *The Journal of Biological Chemistry* 264(19)11401-11406 (1989).
Wesley et al. "PACE/Furin Can Process the Vitamin K-dependent Pro-factor IX Precursor within the Secretory Pathway" *The Journal of Biological Chemistry* 2689(12):8458-8465 (1993).
Watzke et al. "Factor X Santo Domingo Evidence that the Severe Clinical Phenotype Arises from a Mutation Blocking Secretion" *J. Clin. Invest*. 88:1685-1689 (1991).
Wells et al. "Additivity of Mutational Effects in Proteins" *Biochemistry* 29(37):8509-8517 (1990).
Winter et al. "Man-made antibodies" *Nature* 349:293-299 (1991).
Wu et al. "In Vitro γ-Carboxylation of a 59-Residue Recombinant Peptide Including the Propeptide and the γ-Carboxyglutamic Acid Domain of Coagulation Factor IX" *The Journal of Biological Chemistry* 265(22):13124-13129 (1990).
Wu et al. "The Propeptide Binding Site of the Bovine γ-Glutamyl Carboxylase" *The Journal of Biological Chemistry* 272:11718-11722 (1997).
Wu et al. "Identification and purification to near homogeneity of the vitamin K-dependent carboxylase" *Proc. Natl. Acad. Sci. USA* 88:2236-2240 (1991).
Xie et al. "Molecular basis of ethnic differences in drug disposition and response" *Annu Rev Pharmacol Toxicol*. 41:815-50 (2001).
Zhang et al. "Role of Individual γ-Carboxyglutamic Acid Residues of Activated Human Protein C in Defining its In Vitro Anticoagulant Activity" *Blood* 80(4):942-952 (1992).
Zheng et al. "Inhibition of gene expression by anti-sense oligodeoxynucleotides" *Clin. Exp. Immunol*. 100:380-382 (1995).
Zimmermann et al. "Biochemical Basis of Hereditary Resistance to Warfarin in the Rat" *Biochemical Pharmacology* 23:1033-1040 (1974).
Aquilante et al. "Influence of coagulation factor, vitamin K epoxide reductase complex subunit 1, and cytochrome P450 2C9 gene polymorphisms on warfarin dose requirements" *Clinical Pharmacology & Therapeutics* 79(4):291-302 (2006).
Bodin et al. "Cytochrome P450 2C9 (CYP2C9) and vitamin K epoxide reductase (VKORC1) genotypes as determinants of acenocoumarol sensitivity" *Blood* 106(1):135-140 (2005).
D'Andrea et al. "A polymorphism in the VKORC1 gene is associated with an interindividual variability in the dose-anticoagulant effect of warfarin" *Blood* 106(1):645-649 (2005).
Fregin et al. "Homozygosity mapping of a second gene locus for hereditary combined deficiency of vitamin K-dependent clotting factors to the centromeric region of chromosome 16" *Blood* 100(9):3229-3232 (2002).
Gage et al. "Pharmacogenetics and Anticoagulant Therapy" *Journal of Thrombosis and Thrombolysis* 16(1/2):73-78 (2003).
Gage et al. "PharmGKB Submission Update: VIII. PBAT Submission of Genetic Variation in *VKORC1I* to the PharmGKB Network" *Pharmacol Rev* 58(2):138-139 (2006).
Geisen et al. "VKORC1 haplotypes and their impact on the inter-individual and inter-ethnical variability of oral anticoagulation" *Blood* 94(4):773-779 (2005).
Harrington et al. "Pharmacodynamic resistance to warfarin associated with a Val66Met substitution in vitamin K epoxide reductase complex subunit 1" *Thromb Haemost* 93:23-26 (2005).
International Search Report for PCT/US04/31481; date of mailing: Mar. 28, 2005.
Kohn et al. "Natural selection mapping of the warfarin-resistance gene" *PNAS* 97(14):7911-7915 (2000).
Kohn et al. "A gene-anchored map position of the rat warfarin-resistance locus, Rw, and its orthologs in mice and humans" *Blood* 96(5):1996-1998 (2000).
Kohn et al. "Locus-Specific Genetic Differentiation at Rw Among Warfarin-Resistant Rat (*Ratus norvegicus*) Populations" *Genetics* 164:1055-1070 (2003).
Lee et al. "Interethnic variability of warfarin maintenance requirement is explained by *VKORC1* genotype in an Asian population" *Clinical Pharmacology & Therapeutics* 79(3):197-205 (2006).
Li et al. "Identification of the gene for vitamin K epoxide reductase" *Nature* 427:541-544 (2004).
Li et al. "Polymorphisms in the VKORC1 gene are strongly associated with warfarin dosage requirements in patients receiving anticoagulation" *J. Med. Genet*. Online Publication Apr. 12, 2006.
Loebstein et al. Common genetic variants of microsomal epoxide hydrolase affect warfarin dose requirements beyond the effect of cytochrome P450 2C9 *Clinical Pharmacology & Therapeutics* 77(5):365-372 (2005).
Montes et al. "The c.-1639G>A polymorphism of the VKORC1 gene is a major determinant of the response to acenocoumarol in anticoagulated patients" *Br. J. Haematol*. 133(2):183-187 (2006).
Mushiroda et al. "Association of VKORC1 and CYP2C9 polymorphisms with warfarin dose requirements in Japanese patients" *J. Hum. Genet*. 51(3):249-253 (2006).

Pelz et al. "The Genetic Basis of Resistance to Anticoagulants in Rodents" *Genetics* 170:1839-1847 (2005).

Quteineh et al. "Vitamin K epoxide reductase (VKORC1) genetic polymorphism is associated to oral anticoagulant overdose" *Thromb. Haemost.* 94(3):690-691 (2005).

Reider et al. GenBank Accession No. AY 587020 "*Homo sapiens* vitamin K epoxide reductase complex, subunit 1 (VKORC1) gene, complete cds" May 14, 2004.

Reitsma et al. "A C1173T Dimorphism in the VKORC1 Gene Determines Coumarin Sensitivity and Bleeding Risk" *PloS Medicine* 2(10):e312, published on-line Oct. 11, 2005.

Rieder et al. "Effect of VKORC1 Haplotypes on Transcriptional Regulation and Warfarin Dose" *N. Engl J Med* 352(22):2285-2293 (2005).

Rost et al. "Mutations in VKORC1 cause warfarin resistance and multiple coagulation factor deficiency type 2" *Nature* 427:537-541 (2004).

Sconce et al. "The impact of CYP2C9 and VKORC1 genetic polymorphism and patient characteristics upon warfarin dose requirements: proposal for a new dosing regimen" *Blood* 106(7)2329-2333 (2005).

Vecsler et al. "Combined genetic profiles of components and regulators of the vitamin K-dependent γ-carboxylation system affect individual sensitivity to warfarin" *Thromb. Haemost.* 95(2):205-211 (2006).

Veenstra et al. "Association of Vitamin K epoxide reductase complex 1 (VKORC1) variants with warfarin dose in a Hong Kong Chinese patent population" *Pharmacogenetics and Genomics* 15(10):687-691 (2005).

Voora et al. "Use of Pharmacogenetics to Guide Warfarin Therapy" *Drugs of Today* 40(3):247-257 (2004).

Wadelius et al. "Common VKORC1 and GGCX polymorphisms associated with warfarin dose" *The Pharmacogenomics Journal* 5(4):262-270 (2005).

Wallin et al. "A molecular mechanism for genetic warfarin resistance in the rat" *The FASEB Journal* 15:2542-2544 (2001).

Wang et al. "VKORC1 Haplotypes Are Associated With Arterial Vascular Diseases (Stroke, Coronary Heart Disease, and Aortic Dissection)" *Circulation* 113(12):1615-1621, published on-line Mar. 20, 2006.

Yuan et al. "A novel functional VKORC1 promoter polymorphism is associated with inter-individual and inter-ethnic differences in warfarin sensitivity" *Human Molecular Genetics* 14(13):1745-1751 (2005).

Zhao et al. "Novel CYP2C9 genetic variants in Asian subjects and their influence on maintenance warfarin dose" *Clin Pharmacol Ther* 76(3):210-219 (2004).

Horton et al. "Warfarin Therapy: Evolving Strategies in Anticoagulation" *American Family Physician* 59(3):635-646 (1999).

Scott et al. "Warfarin Pharmacogenetics: CYP2C9 and VKORC1 Genotypes Predict Different Sensitivity and Resistance Frequencies in the Ashkenazi and Sephardi Jewish Populations" *American Journal of Human Genetics* 82:495-500 (2008).

Taube et al. "Influence of Cytochrome P-450 CYP2C9 Polymorphisms on Warfarin Sensitivity and Risk of Over-Coagulation in Patients on Long-Term Treatment" *Hemost. Throm. Vasc. Biol.* 96(5):1816-1819 (2000).

Accession AAX84611. Human V201 Coding Sequence. (Sep. 14, 1999) (2 pages).

Accession AAY22213. Human V201 Protein Sequence. (Sep. 14, 1999) (2 pages).

Begent et al. "Characterization and Purification of the Vitamin $K_1$ 2,3 Epoxide Reductase System From Rat Liver" *Journal of Pharmacy and Pharmacology* 53:481-486 (2001).

Restriction Requirement Office Action for U.S. Appl. No. 10/573,131; mailed Jan. 30, 2007 (6 pages).

Non-Final Office Action for U.S. Appl. No. 10/573,131; mailed May 31, 2007 (27 pages).

Non-Final Office Action for U.S. Appl. No. 10/573,131; mailed Jul. 28, 2008 (38 pages).

Non-Final Office Action for U.S. Appl. No. 11/924,707; mailed Apr. 1, 2010 (40 pages).

Communication of a Notice of Opposition dated Oct. 14, 2010 and copy of Opposition Brief, EP Patent No. 1 842 920 BI (EP Application No. 07109353.8).

Office Action issued in Japanese Patent Application No. 2010-151738, dated Nov. 12, 2010.

* cited by examiner

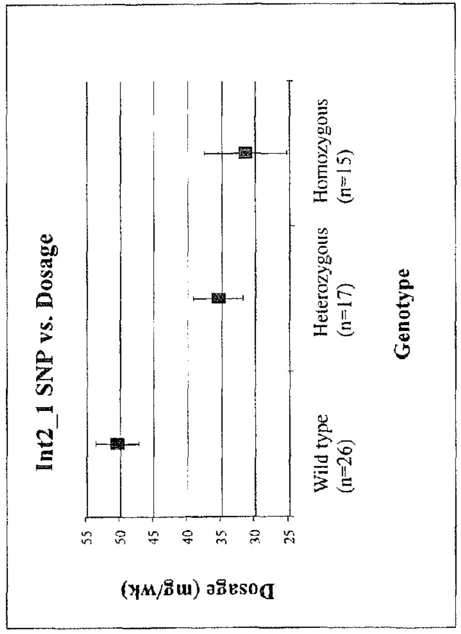
Fig. 1A. vk2581
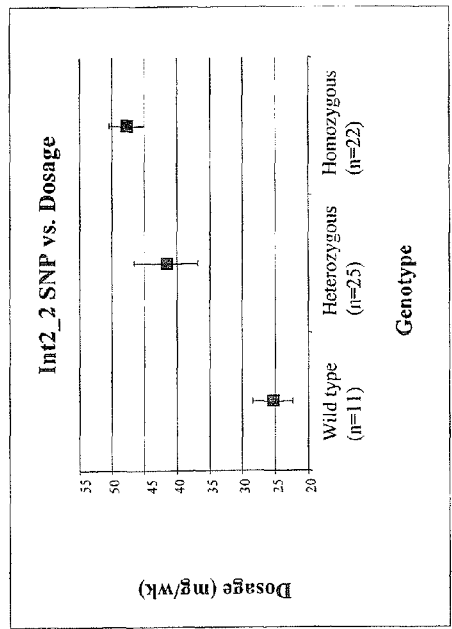
Fig. 1B. vk3294
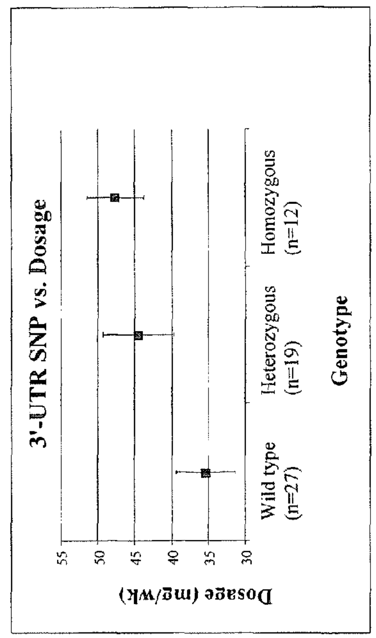
Fig. 1C. vk4769
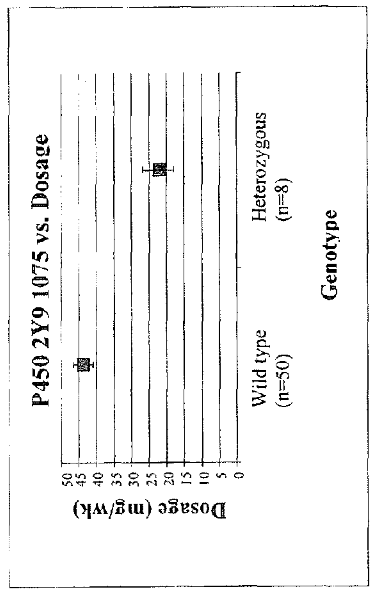
Fig. 1D. p1075

METHODS AND COMPOSITIONS FOR VITAMIN K EPOXIDE REDUCTASE

STATEMENT OF PRIORITY

The present application is a continuation application of U.S. application Ser. No. 10/573,131 filed on Apr. 18, 2006, now U.S Pat. No. 7,687,233, which is a 35 U.S.C. §371 national phase application of PCT Application No. PCT/US2004/031481, having an international filing date of Sep. 23, 2004, which claims the benefit, under 35 U.S.C. §119(e), of U.S. Provisional Application Ser. No. 60/505,527, filed Sep. 23, 2003, the entire contents of each of which are incorporated by reference herein.

GOVERNMENT SUPPORT

The present invention was made, in part, with the support of grant numbers 5P01 HL06350-42 and 5-R01 HL48318 from the National Institutes of Health. The United States Government has certain rights to this invention.

FIELD OF THE INVENTION

The present invention concerns isolated nucleic acids, host cells containing the same, and methods of use thereof, as well as methods and compositions directed to identification of single nucleotide polymorphisms (SNPs) in the Vitamin K epoxide reductase (VKOR) gene and their correlation with sensitivity to warfarin.

BACKGROUND OF THE INVENTION

The function of numerous proteins requires the modification of multiple glutamic acid residues to γ-carboxyglutamate. Among these vitamin K-dependent (VKD) coagulation proteins, FIX (Christmas factor), FVII, and prothrombin are the best known. The observation that a knock-out of the gene for matrix Gla protein results in calcification of the mouse's arteries (Luo et al. (1997) "Spontaneous calcification of arteries and cartilage in mice lacking matrix GLA protein" *Nature* 386:78-81) emphasizes the importance of the vitamin K cycle for proteins with functions other than coagulation. Moreover, Gas6 and other Gla proteins of unknown function are expressed in neural tissue and warfarin exposure in utero results in mental retardation and facial abnormalities. This is consistent with the observation that the expression of VKD carboxylase, the enzyme that accomplishes the Gla modification, is temporally regulated in a tissue-specific manner with high expression in the nervous system during early embryonic stages. Concomitant with carboxylation, reduced vitamin K, a co-substrate of the reaction, is converted to vitamin K epoxide. Because the amount of vitamin K in the human diet is limited, vitamin K epoxide must be converted back to vitamin K by vitamin K epoxide reductase (VKOR) to prevent its depletion. Warfarin, the most widely used anticoagulation drug, targets VKOR and prevents the regeneration of vitamin K. The consequence is a decrease in the concentration of reduced vitamin K, which results in a reduced rate of carboxylation by the γ-glutamyl carboxylase and in the production of undercarboxylated vitamin K-dependent proteins.

In the United States alone, warfarin is prescribed to more than one million patients per year and in Holland, it has been reported that approximately 2% of the population is on long term warfarin therapy. Because the dose of warfarin required for a therapeutic level of anticoagulation varies greatly between patients, the utilization of warfarin is accompanied by a significant risk of side effects. For example, it has been reported that following initiation of warfarin therapy, major bleeding episodes occurred in 1-2% of patients and death occurred in 0.1-0.7% of patients. In spite of the dangers, it has been estimated that warfarin use can prevent 20 strokes per induced bleeding episode and is probably underutilized because of the fear of induced bleeding.

The present invention overcomes previous shortcomings in the art by providing methods and compositions for correlating single nucleotide polymorphisms in a subject with an increased or decreased sensitivity to warfarin, thereby allowing for more accurate and rapid determination of therapeutic and maintenance doses of warfarin at reduced risk to the subject.

SUMMARY OF THE INVENTION

The present invention provides a method of identifying a human subject having increased or decreased sensitivity to warfarin, comprising detecting in the subject the presence of a single nucleotide polymorphism in the VKOR gene, wherein the single nucleotide polymorphism is correlated with increased or decreased sensitivity to warfarin, thereby identifying the subject having increased or decreased sensitivity to warfarin.

Additionally provided is a method of identifying a human subject having increased or decreased sensitivity to warfarin, comprising: a) correlating the presence of a single nucleotide polymorphism in the VKOR gene with increased or decreased sensitivity to warfarin; and b) detecting the single nucleotide polymorphism of step (a) in the subject, thereby identifying a subject having increased or decreased sensitivity to warfarin.

In a further embodiment, the present invention provides a method of identifying a single nucleotide polymorphism in the VKOR gene correlated with increased or decreased sensitivity to warfarin, comprising:

a) identifying a subject having increased or decreased sensitivity to warfarin;

b) detecting in the subject the presence of a single nucleotide polymorphism in the VKOR gene; and c) correlating the presence of the single nucleotide polymorphism of step (b) with the increased or decreased sensitivity to warfarin in the subject, thereby identifying a single nucleotide polymorphism in the VKOR gene correlated with increased or decreased sensitivity to warfarin.

In addition, the present invention provides a method of correlating a single nucleotide polymorphism in the VKOR gene of a subject with increased or decreased sensitivity to warfarin, comprising: a) identifying a subject having increased or decreased sensitivity to warfarin; b) determining the nucleotide sequence of the VKOR gene of the subject of (a); c) comparing the nucleotide sequence of step (b) with the wild type nucleotide sequence of the VKOR gene; d) detecting a single nucleotide polymorphism in the nucleotide sequence of (b); and e) correlating the single nucleotide polymorphism of (d) with increased or decreased sensitivity to warfarin in the subject of (a).

A further aspect of the present invention is an isolated nucleic acid encoding vitamin K epoxide reductase (VKOR), particularly mammalian (e.g., human, ovine, bovine, monkey, etc.) VKOR. Examples include (a) nucleic acids as disclosed herein, such as isolated nucleic acids having the nucleotide sequence as set forth in SEQ ID NO: 8 or SEQ ID NO: 9; (b) nucleic acids that hybridize to isolated nucleic acids of (a) above or the complement thereof (e.g., under stringent conditions), and/or have substantial sequence identity to nucleic acids of (a) above (e.g., are 80, 85, 90 95 or 99% identical to nucleic acids of (a) above), and encode a VKOR; and (c) nucleic acids that differ from the nucleic acids of (a) or (b) above due to the degeneracy of the genetic code, but code for a VKOR encoded by a nucleic acid of (a) or (b) above.

The term "stringent" as used here refers to hybridization conditions that are commonly understood in the art to define the commodities of the hybridization procedure. Stringency conditions can be low, high or medium, as those terms are commonly know in the art and well recognized by one of ordinary skill. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5× Denhardt's solution and 5% dextran sulfate at 42° C., with wash conditions of 25% formamide, 5×SSC and 0.1% SDS at 42° C., to allow hybridization of sequences of about 60% homology. Another example includes hybridization conditions of 6×SSC, 0.1% SDS at about 45° C., followed by wash conditions of 0.2×SSC, 0.1% SDS at 50-65° C. Another example of stringent conditions is represented by a wash stringency of 0.3 M NaCl, 0.03M sodium citrate, 0.1% SDS at 60-70° C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein). In various embodiments, stringent conditions can include, for example, highly stringent (i.e., high stringency) conditions (e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

An additional aspect of the present invention is a recombinant nucleic acid comprising a nucleic acid encoding vitamin K epoxide reductase as described herein operatively associated with a heterologous promoter.

A further aspect of the present invention is a cell that contains and expresses a recombinant nucleic acid as described above. Suitable cells include plant, animal, mammal, insect, yeast and bacterial cells.

A further aspect of the present invention is an oligonucleotide that hybridizes to an isolated nucleic acid encoding VKOR as described herein.

A further aspect of the present invention is isolated and purified VKOR (e.g., VKOR purified to homogeneity) encoded by a nucleic acid as described herein. For example, the VKOR of this invention can comprise the amino acid sequence as set forth in SEQ ID NO:10.

A further aspect of the present invention is a method of making a vitamin K dependent protein which comprises culturing a host cell that expresses a nucleic acid encoding a vitamin K dependent protein in the presence of vitamin K and produces a vitamin K dependent protein, and then harvesting the vitamin K dependent protein from the culture, the host cell containing and expressing a heterologous nucleic acid encoding vitamin K dependent carboxylase, and the host cell further containing and expressing a heterologous nucleic acid encoding vitamin K epoxide reductase (VKOR) and producing VKOR as described herein.

BRIEF DESCRIPTION OF THE DRAWINGS

FIGS. 1A-D Comparisons of warfarin dosages in wild type, heterozygous and homozygous subjects for SNPs vk 2581, vk3294 and vk4769, as well as a comparison of warfarin dosages in wild type and heterozygous subjects for P450 2Y9.

DETAILED DESCRIPTION OF THE INVENTION

Figure 2:
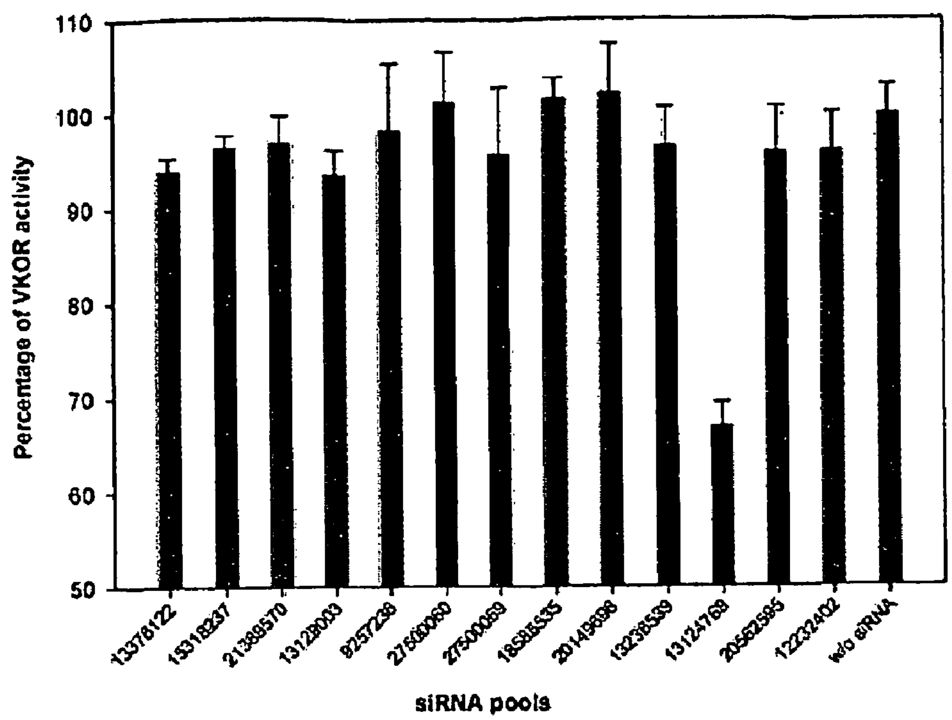
FIG. 2. For each of the 13 siRNA pools, three T7 flasks containing A549 cells were transfected and VKOR activity determined after 72 h. The VKOR assay used 25 μM vitamin Kepoxide. One siRNA pool specific for gene gi:13124769 reduced VKOR activity by 64%-70% in eight repetitions.

As used herein, "a," "an" or "the" can mean one or more than one. For example, "a" cell can mean a single cell or a multiplicity of cells.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The "Sequence Listing" attached hereto forms a part of the instant specification as if fully set forth herein.

The present invention may be carried out based on the instant disclosure and further utilizing methods, components and features known in the art, including but not limited to those described in U.S. Pat. No. 5,268,275 to Stafford and Wu and U.S. Pat. No. 6,531,298 to Stafford and Chang, the disclosures of which are incorporated by reference herein in their entirety as if fully set forth herein.

As used herein, "nucleic acids" encompass both RNA and DNA, including cDNA, genomic DNA, synthetic (e.g., chemically synthesized) DNA and chimeras of RNA and DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid gene encoding an additional polypeptide sequence.

The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

The term "oligonucleotide" refers to a nucleic acid sequence of at least about six nucleotides to about 100 nucleotides, for example, about 15 to 30 nucleotides, or about 20 to 25 nucleotides, which can be used, for example, as a primer in a PCR amplification or as a probe in a hybridization assay or in a microarray. Oligonucleotides may be natural or synthetic, e.g., DNA, RNA, modified backbones, etc.

Where a particular nucleotide sequence is said to have a specific percent identity to a reference nucleotide sequence, the percent identity is relative to the reference nucleotide sequence. For example, a nucleotide sequence that is 50%, 75%, 85%, 90%, 95% or 99% identical to a reference nucleotide sequence that is 100 bases long can have 50, 75, 85, 90, 95 or 99 bases that are completely identical to a 50, 75, 85, 90, 95 or 99 nucleotide sequence of the reference nucleotide sequence. The nucleotide sequence can also be a 100 base long nucleotide sequence that is 50%, 75%, 85%, 90%, 95% or 99% identical to the reference nucleotide sequence over its entire length. Of course, there are other nucleotide sequences that will also meet the same criteria.

A nucleic acid sequence that is "substantially identical" to a VKOR nucleotide sequence is at least 80%, 85% 90%, 95% or 99% identical to the nucleotide sequence of SEQ ID NO:8 or 9. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

As is known in the art, a number of different programs can be used to identify whether a nucleic acid or amino acid has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program that was obtained from Altschul et al., *Methods in Enzymology,* 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al. *Nucleic Acids Res.* 25, 3389-3402.

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

In addition, for sequences that contain either more or fewer nucleotides than the nucleic acids disclosed herein, it is understood that in one embodiment, the percentage of sequence identity will be determined based on the number of identical nucleotides in relation to the total number of nucleotide bases. Thus, for example, sequence identity of sequences shorter than a sequence specifically disclosed herein will be determined using the number of nucleotide bases in the shorter sequence, in one embodiment. In percent identity calculations, relative weight is not assigned to various manifestations of sequence variation, such as, insertions, deletions, substitutions, etc.

The VKOR polypeptides of the invention include, but are not limited to, recombinant polypeptides, synthetic peptides and natural polypeptides. The invention also encompasses nucleic acid sequences that encode forms of VKOR polypeptides in which naturally occurring amino acid sequences are altered or deleted. Preferred nucleic acids encode polypeptides that are soluble under normal physiological conditions. Also within the invention are nucleic acids encoding fusion proteins in which all or a portion of VKOR is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells, or to an HPC4 tag to facilitate purification of polypeptides by affinity chromatography or immunoprecipitation. The invention also includes isolated polypeptides (and the nucleic acids that encode these polypeptides) that include a first portion and a second portion; the first portion includes, e.g., all or a portion of a VKOR polypeptide, and the second portion includes, e.g., a detectable marker.

The fusion partner can be, for example, a polypeptide that facilitates secretion, e.g., a secretory sequence. Such a fused polypeptide is typically referred to as a preprotein. The secretory sequence can be cleaved by the cell to form the mature protein. Also within the invention are nucleic acids that encode VKOR fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequence of SEQ ID NOS: 1-6, 8 or 9 or their complements. In particular embodiments, the hybridizing portion of the hybridizing nucleic acid is typically at least 15 (e.g., 20, 30, or 50) nucleotides in length. The hybridizing portion of the hybridizing nucleic acid is at least 80%, e.g., at least 95%, at least 98% or 100%, identical to the sequence of a portion or all of a nucleic acid encoding a VKOR polypeptide. Hybridizing nucleic acids of the type described herein can be used, for example, as a cloning probe, a primer (e.g., a PCR primer), or a diagnostic probe. Also included within the invention are small inhibitory RNAs (siRNAs) and/or antisense RNAs that inhibit the function of VKOR, as determined, for example, in an activity assay, as described herein and as is known in the art.

In another embodiment, the invention features cells, e.g., transformed cells, which contain a nucleic acid of this invention. A "transformed cell" is a cell into which (or into an ancestor of which) has been introduced, by means of recombinant nucleic acid techniques, a nucleic acid encoding all or a part of a VKOR polypeptide, and/or an antisense nucleic acid or siRNA. Both prokaryotic and eukaryotic cells are included, e.g., bacteria, yeast, insect, mouse, rat, human, plant and the like.

The invention also features nucleic acid constructs (e.g., vectors and plasmids) that include a nucleic acid of the invention that is operably linked to a transcription and/or translation control elements to enable expression, e.g., expression vectors. By "operably linked" is meant that a selected nucleic acid, e.g., a DNA molecule encoding a VKOR polypeptide, is positioned adjacent to one or more regulatory elements, e.g., a promoter, which directs transcription and/or translation of the sequence such that the regulatory elements can control transcription and/or translation of the selected nucleic acid.

The present invention further provides fragments or oligonucleotides of the nucleic acids of this invention, which can be used as primers or probes. Thus, in some embodiments, a fragment or oligonucleotide of this invention is a nucleotide sequence that is at least 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 2000, 2500 or 3000 contiguous nucleotides of the nucleotide sequence set forth in SEQ ID NO:8 or SEQ ID NO:9. Examples of oligonucleotides of this invention are provided in the Sequence Listing included herewith. Such fragments or oligonucleotides can be detectably labeled or modified, for example, to include and/or incorporate a restriction enzyme cleavage site when employed as a primer in an amplification (e.g., PCR) assay.

The invention also features purified or isolated VKOR polypeptides, such as, for example, a polypeptide comprising, consisting essentially of and/or consisting of the amino acid sequence of SEQ ID NO:10 or a biologically active fragment or peptide thereof. Such fragments or peptides are typically at least about ten amino acids of the amino acid sequence of SEQ ID NO:10 (e.g., 15, 20, 25, 30, 35, 40, 45, 50, 55, 60, 65, 75, 85, 95, 100, 125, or 150 amino acids of the amino acid sequence of SEQ ID NO:10) and can be peptides or fragment of contiguous amino acids of the amino acid sequence of the VKOR protein (e.g., as set forth in SEQ ID NO:10). The biological activity of a fragment or peptide of this invention can be determined according to the methods provided herein and as are known in the art for identifying VKOR activity. The fragments and peptides of the VKOR protein of this invention can also be active as antigens for the production of antibodies. The identification of epitopes on a fragment or peptide of this invention is carried out by well known protocols and would be within the ordinary skill of one in the art.

As used herein, both "protein" and "polypeptide" mean any chain of amino acids, regardless of length or post-translational modification (e.g., glycosylation, phosphorylation or N-myristylation). Thus, the term "VKOR polypeptide" includes full-length, naturally occurring VKOR proteins, respectively, as well as recombinantly or synthetically produced polypeptides that correspond to a full-length, naturally occurring VKOR protein, or to a portion of a naturally occurring or synthetic VKOR polypeptide.

A "purified" or "isolated" compound or polypeptide is a composition that is at least 60% by weight the compound of interest, e.g., a VKOR polypeptide or antibody that is separated or substantially free from at least some of the other components of the naturally occurring organism or virus, for example, the cell or viral structural components or other polypeptides or nucleic acids commonly found associated with the polypeptide. As used herein, the "isolated" polypeptide is at least about 25%, 50%, 60%, 70%, 75%, 80%, 85%, 90%, 95%, 97%, 98%, 99% or more pure (w/w). Preferably the preparation is at least 75% (e.g., at least 90% or 99%) by weight the compound of interest. Purity can be measured by any appropriate standard method, e.g., column chromatography, polyacrylamide gel electrophoresis, or HPLC analysis.

Preferred VKOR polypeptides include a sequence substantially identical to all or a portion of a naturally occurring VKOR polypeptide. Polypeptides "substantially identical" to the VKOR polypeptide sequences described herein have an amino acid sequence that is at least 80% or 85% (e.g., 90%, 95% or 99%) identical to the amino acid sequence of the VKOR polypeptides of SEQ ID NO: 10. For purposes of comparison, the length of the reference VKOR polypeptide sequence will generally be at least 16 amino acids, e.g., at least 20, 25, 30, 35, 40, 45, 50, 75, or 100 amino acids.

In the case of polypeptide sequences that are less than 100% identical to a reference sequence, the non-identical positions are preferably, but not necessarily, conservative substitutions for the reference sequence. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, for example, a polypeptide that is 50%, 75%, 85%, 90%, 95% or 99% identical to a reference polypeptide that is 100 amino acids long can be a 50, 75, 85, 90, 95 or 99 amino acid polypeptide that is completely identical to a 50, 75, 85, 90, 95 or 99 amino acid long portion of the reference polypeptide. It can also be a 100 amino acid long polypeptide that is 50%, 75%, 85%, 90%, 95% or 99% identical to the reference polypeptide over its entire length. Of course, other polypeptides also will meet the same criteria.

The invention also features purified or isolated antibodies that specifically bind to a VKOR polypeptide of this invention or to a fragment thereof. By "specifically binds" is meant that an antibody recognizes and binds a particular antigen, e.g., a VKOR polypeptide, or an epitope on a fragment or peptide of a VKOR polypeptide, but does not substantially recognize and bind other molecules in a sample. In one embodiment the antibody is a monoclonal antibody and in other embodiments, the antibody is a polyclonal antibody. The production of both monoclonal and polyclonal antibodies, including chimeric antibodies, humanized antibodies, single chain antibodies, bi-specific antibodies, antibody fragments, etc., is well known in the art.

In another aspect, the invention features a method for detecting a VKOR polypeptide in a sample. This method comprises contacting the sample with an antibody that specifically binds a VKOR polypeptide or a fragment thereof under conditions that allow the formation of a complex between an antibody and VKOR; and detecting the formation of a complex, if any, as detection of a VKOR polypeptide or fragment thereof in the sample. Such immunoassays are well known in the art and include immunoprecipitation assays, immunoblotting assays, immunolabeling assays, ELISA, etc.

The present invention further provides a method of detecting a nucleic acid encoding a VKOR polypeptide in a sample, comprising contacting the sample with a nucleic acid of this invention that encodes VKOR or a fragment thereof, or a complement of a nucleic acid that encodes VKOR or a fragment thereof, under conditions whereby a hybridization complex can form, and detecting formation of a hybridization complex, thereby detecting a nucleic acid encoding a VKOR polypeptide in a sample. Such hybridization assays are well known in the art and include probe detection assays and nucleic acid amplification assays.

Also encompassed by the invention is a method of obtaining a gene related to (i.e., a functional homologue of) the VKOR gene. Such a method entails obtaining or producing a detectably-labeled probe comprising an isolated nucleic acid which encodes all or a portion of VKOR, or a homolog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the VKOR gene.

A further aspect of the present invention is a method of making a vitamin K dependent protein which comprises culturing a host cell that expresses a nucleic acid encoding a vitamin K dependent protein in the presence of vitamin K and produces a vitamin K dependent protein, and then harvesting the vitamin K dependent protein from the culture, the host cell containing and expressing a heterologous nucleic acid encoding vitamin K dependent carboxylase, and the host cell further containing and expressing a heterologous nucleic acid encoding vitamin K epoxide reductase (VKOR) and producing VKOR as described herein. The expression of the VKOR-encoding nucleic acid and the production of the VKOR causes the cell to produce greater levels of the vitamin K dependent protein than would be produced in the absence of the VKOR.

Thus, in some embodiments, the present invention also provides a method of producing a vitamin K dependent protein, comprising:

a) introducing into a cell a nucleic acid that encodes a vitamin K dependent protein under conditions whereby the nucleic acid is expressed and the vitamin K dependent protein is produced in the presence of vitamin K, wherein the cell comprises a heterologous nucleic acid encoding vitamin K dependent carboxylase and further comprises a heterologous nucleic acid encoding vitamin K epoxide reductase; and b) optionally collecting the vitamin K dependent protein from the cell. The vitamin K dependent protein that can be produced can be any vitamin K dependent protein now known or later identified as such, including but not limited to Factor VII, Factor IX, Factor X, Protein C, Protein S and prothrombin, in any combination. Any host cell that can be transformed with the nucleic acids described can be used as described herein, although in some embodiments non-human or even non-mammalian host cells can be used. Nucleic acids encoding vitamin K dependent carboxylase and nucleic acids encoding vitamin K dependent proteins as described herein are well known in the art and their introduction into cells for expression would be carried out according to routine protocols.

Certain embodiments of this invention are based on the inventors' discovery that a subject's therapeutic dose of warfarin for anticoagulation therapy can be correlated with the presence of one or more single nucleotide polymorphisms in the VKOR gene of the subject. Thus, the present invention also provides a method of identifying a human subject having increased or decreased sensitivity to warfarin, comprising detecting in the subject the presence of a single nucleotide polymorphism (SNP) in the VKOR gene, wherein the single nucleotide polymorphism is correlated with increased or decreased sensitivity to warfarin, thereby identifying the subject as having increased or decreased sensitivity to warfarin.

An example of a SNP correlated with an increased sensitivity to warfarin is a G→C alteration at nucleotide 2581 (SEQ ID NO:12) (in intron 2 of the VKOR gene; GenBank accession no. refSNP ID: rs8050894, incorporated by reference herein) of the nucleotide sequence of SEQ ID NO:11, which is a reference sequence encompassing the genomic sequence of SEQ ID NO:8 and approximately 1000 nucleotides preceding and following this sequence. This sequence can be located as having the genome position "human chromosome 16p11.2" or in the physical map in the NCBI database as human chromosome 16: 31009700-31013800.

Examples of SNPs correlated with a decreased sensitivity to warfarin are a T→C alteration at nucleotide 3294 (SEQ ID NO:13) (in intron 2 of the VKOR gene; GenBank accession no. refSNP ID: rs2359612, incorporated by reference herein) of the nucleotide sequence of SEQ ID NO:11 and a G→A alteration at nucleotide 4769 (SEQ ID NO:14) (in the 3' UTR of the VKOR gene; GenBank accession no. refSNP ID: rs7294, incorporated by reference herein) of the nucleotide sequence of SEQ ID NO:11.

As used herein, a subject having an "increased sensitivity to warfarin" is a subject for whom a suitable therapeutic or maintenance dose of warfarin is lower than the therapeutic or maintenance dose of warfarin that would suitable for a normal subject, i.e., a subject who did not carry a SNP in the VKOR gene that imparts a phenotype of increased sensitivity to warfarin. Conversely, as used herein, a subject having a "decreased sensitivity to warfarin" is a subject for whom a suitable therapeutic or maintenance dose of warfarin is higher than the therapeutic or maintenance dose of warfarin that would suitable for a normal subject, i.e., a subject who did not carry a SNP in the VKOR gene that imparts a phenotype of decreased sensitivity to warfarin. An example of a typical therapeutic dose of warfarin for a normal subject is 35 mg per week, although this amount can vary (e.g., a dose range of 3.5 to 420 mg per week is described in Aithal et al. (1999) *Lancet* 353:717-719). A typical therapeutic dose of warfarin can be determined for a given study group according to the methods described herein, which can be used to identify subjects with therapeutic warfarin doses above or below this dose, thereby identifying subjects having decreased or increased sensitivity to warfarin.

Further provided herein is a method of identifying a human subject having increased or decreased sensitivity to warfarin, comprising: a) correlating the presence of a single nucleotide polymorphism in the VKOR gene with increased or decreased sensitivity to warfarin; and b) detecting the single nucleotide polymorphism of step (a) in the subject, thereby identifying a subject having increased or decreased sensitivity to warfarin.

In addition, the present invention provides a method of identifying a single nucleotide polymorphism in the VKOR gene correlated with increased or decreased sensitivity to warfarin, comprising: a) identifying a subject having increased or decreased sensitivity to warfarin; b) detecting in the subject the presence of a single nucleotide polymorphism in the VKOR gene; and c) correlating the presence of the single nucleotide polymorphism of step (b) with the increased or decreased sensitivity to warfarin in the subject, thereby identifying a single nucleotide polymorphism in the VKOR gene correlated with increased or decreased sensitivity to warfarin.

Also provided herein is a method of correlating a single nucleotide polymorphism in the VKOR gene of a subject with increased or decreased sensitivity to warfarin, comprising: a) identifying a subject having increased or decreased sensitivity to warfarin; b) determining the nucleotide sequence of the VKOR gene of the subject of (a); c) comparing the nucleotide sequence of step (b) with the wild type nucleotide sequence of the VKOR gene; d) detecting a single nucleotide polymorphism in the nucleotide sequence of (b); and e) correlating the single nucleotide polymorphism of (d) with increased or decreased sensitivity to warfarin in the subject of (a).

A subject is identified as having an increased or decreased sensitivity to warfarin by establishing a therapeutic or maintenance dose of warfarin for anticoagulation therapy according to well known protocols and comparing the therapeutic or maintenance dose for that subject with the therapeutic or maintenance dose of warfarin for anticoagulation therapy of a population of normal subjects (e.g., subjects lacking any SNPs in the VKOR gene correlated with increased or decreased sensitivity to warfarin) from which an average or mean therapeutic or maintenance dose of warfarin is calculated. A subject having a therapeutic or maintenance dose of warfarin that is below the average therapeutic or maintenance dose of warfarin (e.g., the dose of warfarin that is therapeutic or provides a maintenance level for a subject that has a wild type VKOR gene, i.e., lacking any single nucleotide polymorphisms associated with warfarin sensitivity) is a subject identified as having an increased sensitivity to warfarin. A subject having a therapeutic or maintenance dose of warfarin that is above the average therapeutic or maintenance of warfarin is a subject identified as having a decreased sensitivity to warfarin. An average therapeutic or maintenance dose of warfarin for a subject with a wild type VKOR gene would be readily determined by one skilled in the art.

The nucleotide sequence of the VKOR gene of a subject is determined according to methods standard in the art, and as described in the Examples provided herein. For example, genomic DNA is extracted from cells of a subject and the VKOR gene is located and sequenced according to known protocols. Single nucleotide polymorphisms in the VKOR gene are identified by a comparison of a subject's sequence with the wild type sequence as known in the art (e.g., the reference sequence as shown herein as SEQ ID NO:11).

A SNP in the VKOR gene is correlated with an increased or decreased sensitivity to warfarin by identifying the presence of a SNP or multiple SNPs in the VKOR gene of a subject also identified as having increased or decreased sensitivity to warfarin, i.e., having a maintenance or therapeutic dose of warfarin that is above or below the average dose and performing a statistical analysis of the association of the SNP or SNPs with the increased or decreased sensitivity to warfarin, according to well known methods of statistical analysis. An analysis that identifies a statistical association (e.g., a significant association) between the SNP(s) (genotype) and increased or decreased warfarin sensitivity (phenotype) establishes a correlation between the presence of the SNP(s) in a subject and an increased or decreased sensitivity to warfarin in that subject.

It is contemplated that a combination of factors, including the presence of one or more SNPs in the VKOR gene of a subject, can be correlated with an increased or decreased sensitivity to warfarin in that subject. Such factors can include, but are not limited to cytochrome p450 2C9 polymorphisms, race, age, gender, smoking history and hepatic disease.

Thus, in a further embodiment, the present invention provides a method of identifying a human subject having increased or decreased sensitivity to warfarin, comprising identifying in the subject the presence of a combination of factors correlated with an increased or decreased sensitivity to warfarin selected from the group consisting of one or more single nucleotide polymorphisms of the VKOR gene, one or more cytochrome p450 2C9 polymorphisms, race, age, gender, smoking history, hepatic disease and any combination of two or more of these factors, wherein the combination of factors is correlated with increased or decreased sensitivity to warfarin, thereby identifying the subject having increased or decreased sensitivity to warfarin.

Further provided herein is a method of identifying a human subject having increased or decreased sensitivity to warfarin, comprising: a) correlating the presence of a combination of factors with an increased or decreased sensitivity to warfarin, wherein the factors are selected from the group consisting of one or more single nucleotide polymorphisms of the VKOR gene, one or more cytochrome p450 2C9 polymorphisms, race, age, gender, smoking history, hepatic disease and any combination of two or more of these factors; and b) detecting the combination of factors of step (a) in the subject, thereby identifying a subject having increased or decreased sensitivity to warfarin.

In addition, the present invention provides a method of identifying a combination of factors correlated with an increased or decreased sensitivity to warfarin, wherein the factors are selected from the group consisting of one or more single nucleotide polymorphisms of the VKOR gene, one or more cytochrome p450 2C9 polymorphisms, race, age, gender, smoking history, hepatic disease and any combination of two or more of these factors, comprising: a) identifying a subject having increased or decreased sensitivity to warfarin; b) detecting in the subject the presence of a combination of the factors; and c) correlating the presence of the combination of factors of step (b) with the increased or decreased sensitivity to warfarin in the subject, thereby identifying a combination of factors correlated with increased or decreased sensitivity to warfarin.

Also provided herein is a method of correlating a combination of factors, wherein the factors are selected from the group consisting of one or more single nucleotide polymorphisms of the VKOR gene, one or more cytochrome p450 2C9 polymorphisms, race, age, gender, smoking history, hepatic disease and any combination of two or more of these factors, with increased or decreased sensitivity to warfarin, comprising: a) identifying a subject having increased or decreased sensitivity to warfarin; b) identifying the presence of a combination of the factors in the subject; and c) correlating the combination of the factors of (b) with increased or decreased sensitivity to warfarin in the subject of (a).

A combination of factors as described herein is correlated with an increased or decreased sensitivity to warfarin by identifying the presence of the combination of factors in a subject also identified as having increased or decreased sensitivity to warfarin and performing a statistical analysis of the association of the combination of factors with the increased or decreased sensitivity to warfarin, according to well known methods of statistical analysis. An analysis that identifies a statistical association (e.g., a significant association) between the combination of factors and the warfarin sensitivity phenotype (increased or decreased) establishes a correlation between the presence of the combination of factors in a subject and an increased or decreased sensitivity to warfarin in that subject.

Further provided herein are nucleic acids encoding VKOR and comprising one or more SNPs as described herein. Thus, the present invention further provides nucleic acids comprising, consisting essentially of and/or consisting of the nucleotide sequence as set forth in SEQ ID NOs:12, 13, 14, 15 and 16. The nucleic acids can be present in a vector and the vector can be present in a cell. Further included are proteins encoded by a nucleic acid comprising a nucleotide sequence as set forth in SEQ ID NOs:12, 13, 14, 15 and 16, as well as antibodies that specifically bind a protein encoded by a nucleic acid comprising a nucleotide sequence as set forth in SEQ ID NOs:12, 13, 14, 15 and 16. The present invention is more particularly described in the following examples that are intended as illustrative only since numerous modifications and variations therein will be apparent to those skilled in the art.

EXAMPLES

Example 1

Correlation Between SNPS in VKOR Gene and Increased or Decreased Sensitivity to Warfarin The most prevalent isoform of the VKOR gene is about 4 kb long, has three exons and encodes an enzyme of 163 amino acids with a mass of 18.4 kDa. In the present study, three mutations vk2581 (G>C), vk3294(T>C) and vk4769(G>A), identified as SNPs (heterozygosity ratios of 46.9%, 46.8% and 46.3%, respectively) were examined for a correlation between their presence in a subject and the maintenance dose of warfarin required to achieve a therapeutically effective response.

1. Selection of Subjects

Subjects were obtained from the UNC Coagulation Clinic in the Ambulatory Care Center. Informed consent was obtained by a trained genetic counselor. Subjects not fluent in English were excluded because of the lack of translators and the requirement for consent. To qualify for the study, subjects had warfarin for at least six months, were older than 18 and were followed by the UNC Coagulation clinic at the Ambulatory Care Clinic.

2. Extraction of Genomic DNA from Whole Blood

Genomic DNAs were extracted from the whole blood of subjects using QlAamp DNA Blood Mini Kit (QIAGEN cat#51104). The DNA concentration was adjusted to 10 ng/μL.

3. Sequencing of the Genomic DNA Samples

Approximately 10 ng of DNA was used for polymerase chain reaction (PCR) assays. The primers used to amplify the VKOR gene were: Exon 1-5' CCAATCGCCGAGTCAGAGG (SEQ ID NO:29) and Exon 1-3' CCCAGTCCCCAGCACTGTCT (SEQ ID NO:30) for the 5'-UTR and Exon 1 region; Exon 2-5' AGGGGAGGATAGGGTCAGTG (SEQ ID NO:31) and Exon 2-3' CCTGTTAGTTACCTCCCCACA (SEQ ID NO:32) for the Exon 2 region; and Exon 3-5' ATACGTGCGTAAGCCACCAC (SEQ ID NO:33) and Exon 3-3' ACCCAGATATGCCCCCTTAG (SEQ ID NO:34) for the Exon3 and 3'-UTR region. Automated high throughput capillary electrophoresis DNA sequencing was used for detecting SNPs in the VKOR gene.

4. Detection of known SNPs Using Real-Time PCR

The assay reagents for SNP genotyping were from the Assay-by-Design™ service (Applied Biosystems, cat#4332072). The primers and probes (FAM™ and VIC™ dye-labeled) were designed using Primer Express software and were synthesized in an Applied Biosystems synthesizer. The primer pairs for each SNP are located at the upstream/downstream position of the SNP site and can generate less than 100 bp length of a DNA fragment in the PCR reaction. The FAM™ and VIC™ dye-labeled probes were designed to cover the SNP sites with a length of 15-16 nt. The primer and probe sequences for each VKOR SNP are shown in Table 2.

The 2× TaqMan™ Universal PCR Master Mix, No AmpErase UNG (Applied Biosystems, cat#432-4018) was used in the PCR reactions. Forty cycles of real-time PCR were performed in an Opticon II (MJ Research) machine. There was a 10 minute 95° C. preheat followed by 92° C. for 15 sec, 600° C. for 1 min. and then a plate reading. The results were read according to the signal value of FAM and VIC dye.

5. Statistical Analysis

The difference of average dose between different genotypes was compared by analysis of variance (ANOVA) using SAS version 8.0 (SAS, Inc., Cary, N.C.). A two-sided p value less than 0.05 was considered significant. Examination of the distribution and residuals for the average dose of treatment among the SNP groups indicated that a log transformation was necessary to satisfy the assumption of homogeneity of variance.

6. Correlation of SNPs with Warfarin Dosage

By direct genomic DNA sequencing and SNP real-time PCR detection, five SNPs were identified in the VKOR gene: one in the 5'-UTR, two in intron II, one in the coding region and one in the 3'-UTR (Table 1).

Among these SNPs, the vk563 and vk4501 SNPs allele were carried by only one of the 58 subjects of the study (a triple heterozygous, also carrying the 3'-UTR SNP allele), while the other SNPs were identified in 17-25 heterozygous patients.

Each marker was first analyzed independently. FIG. 1A shows that the average warfarin dose for patients with the vk2581 wild type allele was 50.19±3.20 mg per week (n=26), while those heterozygous and homozygous for this polymorphism were 35.19±3.73 (n=17) and 31.14±6.2 mg perweek (n=15), respectively. FIG. 1B shows that the average warfarin dose for patients with the wild-type vk3294 allele was 25.29±3.05 mg per week (n=11), while patients bearing the heterozygous and homozygous alleles were 41.68±4.92 (n=25) and 47.73±2.75 mg per week (n=22), respectively. FIG. 1C shows the average warfarin dose for patients with vk4769 SNP wild type was 35.35±4.01 mg per week (n=27), while patients with the heterozygous and homozygous alleles required 44.48±4.80 (n=19) and 47.56±3.86 mg per week (n=12), respectively. It was also observed that P450 2C9 *3 has a significant effect on warfarin dose (FIG. 1D), as previously reported (Joffe et al. (2004) "Warfarin dosing and cytochrome P450 2C9 polymorphisms" *Thromb Haemost* 91:1123-1128). The average warfarin dose for patients with P450 2C9 *1 (wild type) was 43.82±2.75 mg per week (n=50), while patients heterozygous for this allele required 22.4±4.34 mg per week (n=8).

7. Statistical Analysis

The association of the Loge (warfarin average dosage) (LnDose) with the SNPs in the VKOR gene was examined by analysis of variance (ANOVA). SAS was used first to do a repeated procedure in which a series of factors (race, gender, smoking history, hepatic diseases, SNPs at cytochrome P450 2Y9 gene, etc.) were examined to identify factors, excluding VKOR SNPs, which might affect dosage. P450 2C9 *3 was significantly associated with the average dose of warfarin; thus, it was included as a covariant for further analysis. The analysis indicated that the three VKOR SNPs were still significantly associated with weekly warfarin dose (vk2581, $P<0.0001$; vk3294, $P<0.0001$; and vk4769, $P=0.0044$), when the covariance is included.

To specifically test if the three SNPs of VKOR were independently associated with warfarin dosage, the analysis was repeated in which two SNPs in the VKOR gene were included as covariates for the other SNP. The three VKOR SNPs are located within 2 kb distance of one another and are expected to be closely linked. It was clear from inspection that, at least for Caucasians, one haplotype (where A=vk2581 guanine and a=vk2581 cytosine; B=vk3294 thymine and b=vk3924 cytosine; C=vk4769 guanine and c=vk4769 adenine) was AAbbcc and another aaBBCC. The distribution of individual SNPs in patients was found to be significantly correlated with the others ($R=0.63-0.87$, $p<0.001$). Indeed, subjects with the haplotype AAbbcc (n=7) required a significantly higher dosage of warfarin (warfarin dosage=48.98±3.93) compared to those patients with haplotype aaBBCC (25.29±3.05; $p<0.001$).

Example 2 siRNA Design and Synthesis siRNAs were Selected using an advanced version of a rational design algorithm (Reynolds et al. (2004) "Rational siRNA design for RNA interference" *Nature Biotechnology* 22:326-330). For each of the 13 genes, four siRNAs duplexes with the highest scores were selected and a BLAST search was conducted using the Human EST database. To minimize the potential for off-target silencing effects, only those sequence targets with more than three mismatches against un-related sequences were selected (Jackson et al. (2003) "Expression profiling reveals off-target gene regulation by RNAi" *Nat Biotechnol* 21:635-7). All duplexes were synthesized in Dharmacon (Lafayette, Colo.) as 21-mers with UU overhangs using a modified method of 2'-ACE chemistry (Scaringe (2000) "Advanced 5'-silyl-2'-orthoester approach to RNA oligonucleotide synthesis" *Methods Enzymol* 317:3-18) and the AS strand was chemically phosphorylated to ensure maximum activity (Martinez et al. (2002) "Single-stranded antisense siRNAs guide target RNA cleavage in RNAi" *Cell* 110:563-74).

Example 3 siRNA Transfection

Transfection was essentially as previously described (Harborth et al. (2001) "Identification of essential genes in cultured mammalian cells using small interfering RNAs" *J Cell Sci* 114:4557-65) with minor modifications.

Example 4

VKOR Activity Assay siRNA transfected A549 cells were trypsinized and washed twice with cold PBS. $1.5\times10^7$ cells were taken for each VKOR assay. 200 μL buffer D (250 mM $Na_2HPO_4$-$NaH_2PO_4$, 500 mM KCl, 20% glycerol and 0.75% CHAPS, pH 7.4) was added to the cell pellet, followed by sonication of the cell lysate. For assays of solubilized microsomes, microsomes were prepared from $2\times10^9$ cells as described (Lin et al. (2002) "The putative vitamin K-dependent gamma-glutamyl carboxylase internal propeptide appears to be the propeptide binding site" *J Biol Chem* 277:28584-91); 10 to 50 μL of solubilized microsomes were used for each assay. Vitamin K epoxide was added to the concentration indicated in the figure legends and DTT was added to 4 mM to initiate the reaction. The reaction mixture was incubated in yellow light at 30° C. for 30 minutes and stopped by adding 500 μL 0.05 M $AgNO_3$:isopropanol (5:9). 500 μL hexane was added and the mixture was vortexed vigorously for 1 minute to extract the vitamin K and KO. After 5 minutes centrifugation, the upper organic layer was transferred to a 5-mL brown vial and dried with $N_2$. 150 μL HPLC buffer, acetonitrile:isopropanol:water (100:7:2), was added to dissolve the vitamin K and KO and the sample was analyzed by HPLC on an A C-18 column (Vydac, cat#218TP54).

Example 5

RT-qPCR (Reverse Transcriptase Quantitative PCR)

$1\times10^6$ cells were washed with PBS twice and total RNA was isolated with Trizol reagent according to the manufacturer's protocol (Invitrogen). 1 μg of RNA was digested by RQ1 DNaseI (Promega) and heat-inactivated. First strand cDNA was made with M-MLV reverse transcriptase (Invitrogen). cDNAs were mixed with DyNAmo SYBR Green qPCR pre-mix (Finnzymes) and real-time PCR was performed with an Opticon II PCR thermal cycler (MJ Research). The following primers were used:

```
13124769-5'(F):
(TCCAACAGCATATTCGGTTGC, SEQ ID NO: 1);

13124769-3 (R)':
(TTCTTGGACCTTCCGGAAACT, SEQ ID NO: 2);

GAPDH-F:
(GAAGGTGAAGGTCGGAGTC, SEQ ID NO: 3);

GAPDH-R:
(GAAGATGGTGATGGGATTTC, SEQ ID NO: 4);
```

-continued

```
Lamin-RT-F:
(CTAGGTGAGGCCAAGAAGCAA, SEQ ID NO: 5)
and

Lamin-RT-R:
(CTGTTCCTCTCAGCAGACTGC, SEQ ID NO: 6).
```

Example 6

Over-Expression of VKOR in Sf9 Insect Cell Line

The cDNA for the mGC11276 coding region was cloned into pVL1392 (Pharmingen), with the HPC4 tag (EDQVDPRLIDGK, SEQ ID NO: 7) at its amino terminus and expressed in Sf9 cells as described (Li et al. (2000) "Identification of a *Drosophila* vitamin K-dependent gamma-glutamyl carboxylase" *J Biol Chem* 275:18291-6).

Example 7

Gene Selection

The search for the VKOR gene was focused on human chromosome sixteen between markers D16S3131 and D16S419. This region corresponds to chromosome 16 at 50cM-65cM on the genetic map and 26-46.3 Mb on the physical map. 190 predicted coding sequences in this region were analyzed by a BLASTX search of the NCBI non-redundant protein database. Those human genes and orthologs from related species with known function were eliminated. Because VKOR appears to be a transmembrane protein (Carlisle & Suttie (1980) "Vitamin K dependent carboxylase: subcellular location of the carboxylase and enzymes involved in vitamin K metabolism in rat liver" *Biochemistry* 19:1161-7), the remaining genes were translated according to the cDNA sequences in the NCBI database and analyzed with the programs TMHMM and TMAP (Biology WorkBench, San Diego Supercomputer System) to predict those with transmembrane domains. Thirteen genes predicted to code for integral membrane proteins were chosen for further analysis.

Example 8

Cell Line Screening for VKOR Activity

The strategy was to identify a cell line expressing relatively high amounts of VKOR activity and use siRNA to systematically knock down all thirteen candidate genes. siRNA, double stranded RNA of 21-23 nucleotides, has been shown to cause specific RNA degradation in cell culture (Hara et al. (2002) "Raptor, a binding partner of target of rapamycin (TOR), mediates TOR action" *Cell* 110:177-89; Krichevsky & Kosik (2002) "RNAi functions in cultured mammalian neurons" *Proc Natl Acad Sci USA* 99:11926-9; Burns et al. (2003) "Silencing of the Novel p53 Target Gene Snk/Plk2 Leads to Mitotic Catastrophe in Paclitaxel (Taxol)-Exposed Cells" *Mol Cell Biol* 23:5556-71). However, application of siRNA for large scale screening in mammalian cells has not previously been reported because of the difficulty in identifying a functional target for a specific mammalian cell mRNA (Holen et al. (2003) "Similar behaviour of single-strand and double-strand siRNAs suggests they act through a common RNAi pathway" *Nucleic Acids Res* 31:2401-7). The development of a rational selection algorithm (Reynolds et al.) for siRNA design increases the probability that a specific siRNA can be developed; furthermore, the probability of success can be increased by pooling four rationally selected siRNAs. Using siRNA to search for previously unidentified genes has the advantage that, even if VKOR activity requires the product of more than one gene for activity, the screen should still be effective because the assay determines the loss of enzymatic activity.

Fifteen cell lines were screened and a human lung carcinoma line, A549, was identified to exhibit sufficient warfarin-sensitive VKOR activity for facile measurement. A second human colorectal adenocarcinoma cell line, HT29, which expressed very little VKOR activity, was used as a reference.

Example 9 siRNA Inhibition of VKOR Activity in A549 Cells

Each of the thirteen pools of siRNA were transfected in triplicate into A549 cells and assayed for VKOR activity after 72 hours. One siRNA pool specific for gene gi:13124769 reduced VKOR activity by 64%-70% in eight separate assays (FIG. 2).

Figure 3:
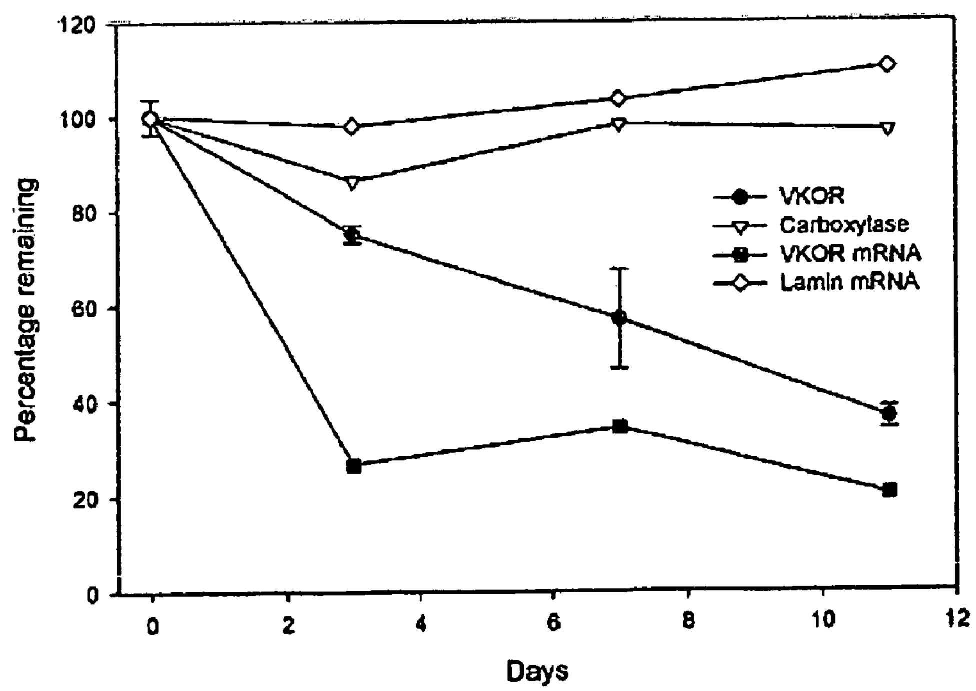
FIG. 3. Time course of inhibition of VKOR activity by the siRNA pool specific for gi:13124769 in A549 cells. VKOR activity decreased continuously during this time period while the level of its mRNA decreased rapidly to about 20% of normal. 25 μM vitamin K epoxide was used for this assay. The siRNA did not affect the activity of VKD carboxylase or the level of lamin A/C mRNA.

One possible reason that VKOR activity was inhibited to only ~35% of its initial activity after 72 hours is that the half-life of mammalian proteins varies greatly (from minutes to days) (Zhang et al. (1996) "The major calpain isozymes are long-lived proteins. Design of an antisense strategy for calpain depletion in cultured cells" *J Biol Chem* 271:18825-30; Bohley (1996) "Surface hydrophobicity and intracellular degradation of proteins" *Biol Chem* 377:425-35; Dice & Goldberg (1975) "Relationship between in vivo degradative rates and isoelectric points of proteins" *Proc Natl Acad Sci USA* 72:3893-7), and mRNA translation is being inhibited, not enzyme activity. Therefore, the cells were carried through eleven days and their VKOR activity followed. FIG. 3 shows that the level of mRNA for gi:13124769 mRNA decreased rapidly to about 20% of normal while VKOR activity decreased continuously during this time period. This reduction in activity is not a general effect of the siRNA or the result of cell death because the level of VKD carboxylase activity and lamin A/C mRNA remained constant. Furthermore, the level of gi:132124769 mRNA is four fold lower in HT-29 cells, which have low VKOR activity, than in A549 cells that exhibit high VKOR activity. These data indicate that gi:13124769 corresponds to the VKOR gene.

Example 10

Identification of Gene Encoding VKOR

The gene, IMAGE 3455200 (gi:13124769, SEQ ID NO: 8), identified herein to encode VKOR, maps to human chromosome 16p11.2, mouse chromosome 7F3, and rat chromosome 1:180.8 Mb. There are 338 cDNA clones in the NCBI database representing seven different splicing patterns (NCBI AceView program). These are composed of all or part of two to four exons. Among these, the most prevalent isoform, mGC11276, has three exons and is expressed at high levels in lung and liver cells. This three exon transcript (SEQ ID NO: 9) encodes a predicted protein of 163 amino acids with a mass of 18.2 kDa (SEQ ID NO: 10). It is a putative N-myristylated endoplasmic reticulum protein with one to three transmembrane domains, depending upon the program used for prediction. It has seven cysteine residues, which is consistent with observations that the enzymatic activity is dependent upon thiol reagents (Thijssen et al. (1994) "Microsomal lipoamide reductase provides vitamin K epoxide reductase with reducing equivalents" *Biochem J* 297:277-80). Five of the seven cysteines are conserved among human, mice, rat, zebrafish, *Xenopus* and *Anopheles*.

Figure 4:
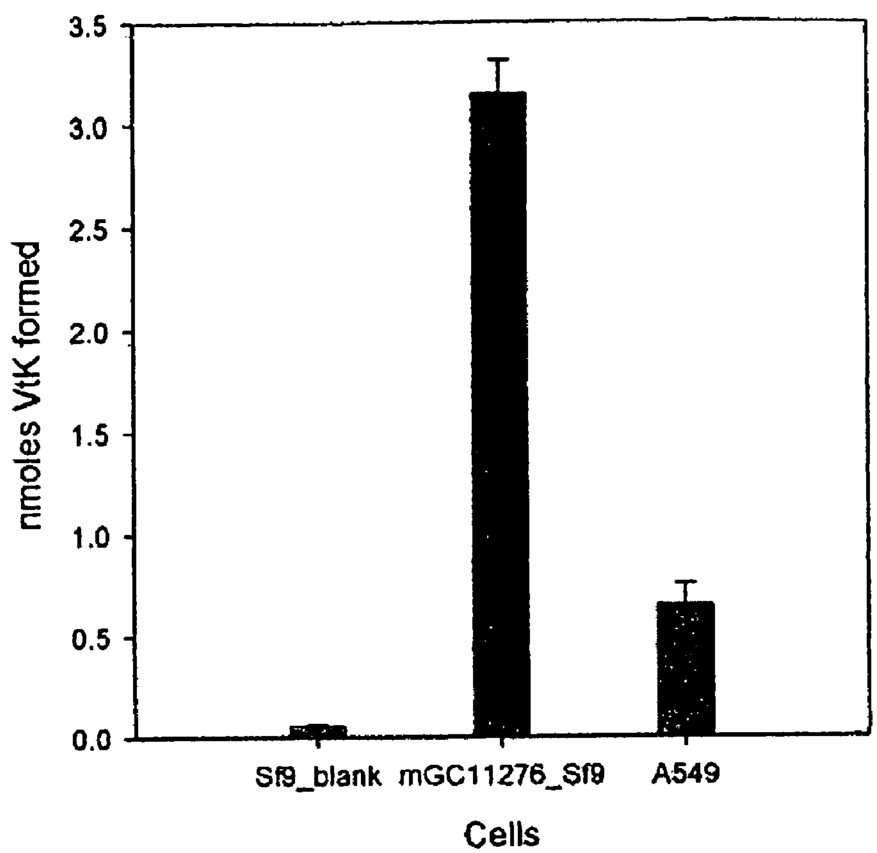
FIG. 4. VKOR activity was detected when mGC__11276 was expressed in Sf9 insect cells. ~$1\times10^6$ cells were used in this assay. Reactions were performed using 32 μM KO at 30° C. for 30 minutes in Buffer D. Blank Sf9 cells served as a negative control and A549 cells as a reference.

To confirm that the VKOR gene had been identified, the most prevalent form of the enzyme (three exons) was expressed in *Spodoptera frugiperda, Sf9* cells. Sf9 cells have no measurable VKOR activity but exhibit warfarin sensitive activity when transfected with mGC11276 cDNA (FIG. 4). VKOR activity is observed from constructs with an epitope tag at either their amino or carboxyl terminus. This tag should assist in the purification of VKOR.

Figure 5:
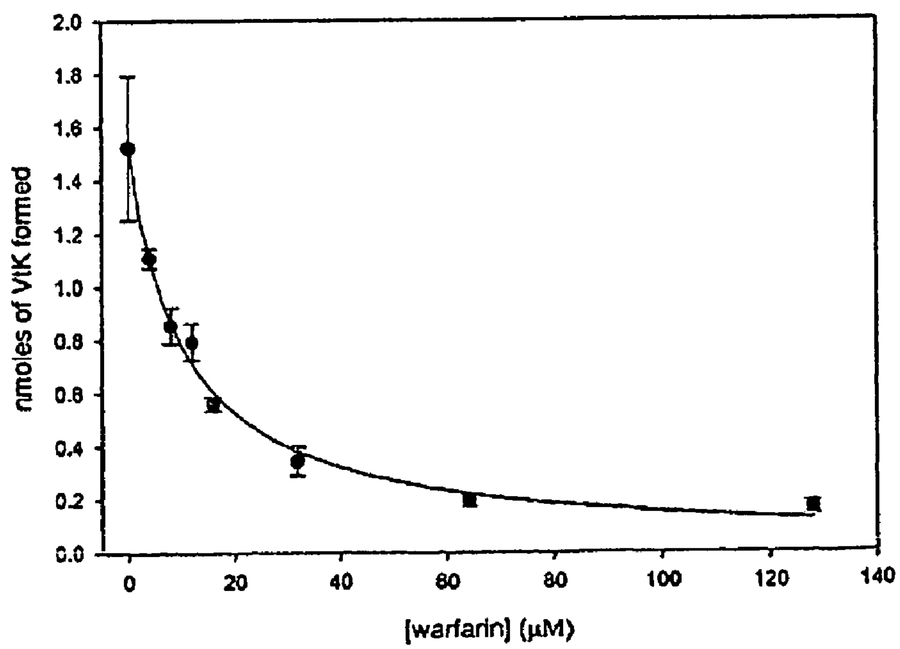
FIG. 5. Inhibition of VKOR by warfarin. Reactions were performed using 1.6 mg microsomal proteins made from VKOR_Sf9 cells, 60 μM KO, and various concentration of warfarin at 30° C. for 15 minutes in Buffer D.

VKOR should exhibit warfarin sensitivity, therefore microsomes were made from Sf9 cells expressing VKOR and tested for warfarin sensitivity. The VKOR activity is warfarin-sensitive (FIG. 5).

In summary, the present invention provides the first example of using siRNA in mammalian cells to identify an unknown gene. The identity of the VKOR gene was confirmed by its expression in insect cells. The VKOR gene encodes several isoforms. It will be important to characterize the activity and expression pattern of each isoform. Millions of people world-wide utilize warfarin to inhibit coagulation; therefore it is important to further characterize VKOR as it can lead to more accurate dosing or design of safer, more effective, anti-coagulants.

The foregoing is illustrative of the present invention, and is not to be construed as limiting thereof. The invention is defined by the following claims, with equivalents of the claims to be included therein.

All publications, patent applications, patents, patent publications and other references cited herein are incorporated by reference in their entireties for the teachings relevant to the sentence and/or paragraph in which the reference is presented.

TABLE 1

Five SNPs examined in VKOR gene

| SNPs | position | AA change | Heterozygous ratio |
|---|---|---|---|
| vk563 G > A (SEQ ID NO: 15) | 5'-UTR | N/A | 1/58 |
| vk2581 G > C (SEQ ID NO: 12) | Intron2 | N/A | 17/58 |
| vk3294 T > C (SEQ ID NO: 13) | Intron2 | N/A | 25/58 |
| vk4501 C > T (SEQ ID NO: 16 | Exon3 | Leu120Leu | 1/58 |
| vk4769 G > A (SEQ ID NO: 14 | 3'-UTR | N/A | 19/58 |

TABLE 2

| SNPs | VIC Probe Sequence | FAM Probe Sequence | Forward Primer | Reverse Primer |
|---|---|---|---|---|
| vk2581 G > C | TCATCACGGAGCGTC (SEQ ID NO: 17) | TCATCACCGAGCGTC (SEQ ID NO: 18) | GGTGATCCACACAGCTGACA (SEQ ID NO: 19) | CCTGTTAGTTACCTCCCCACATC (SEQ ID NO: 20) |
| vk3294 T > C | CCAGGACCATGGTGC (SEQ ID NO: 21) | CCAGGACCGTGGTGC (SEQ ID NO: 22) | GCTCCAGAGAAGGCATCACT (SEQ ID NO: 23) | GCCAAGTCTGAACCATGTGTCA (SEQ ID NO: 24) |
| vk4769 G > A | ATACCCGCACATGAC (SEQ ID NO: 25) | CATACCCACACATGAC (SEQ ID NO: 26) | GTCCCTAGAAGGCCCTAGATGT (SEQ ID NO: 27) | GTGTGGCACATTTGGTCCATT (SEQ ID NO: 28) |

That which is claimed is:

1. A method of identifying a human subject having decreased sensitivity to warfarin, comprising detecting in the subject the presence of an allele of a single nucleotide polymorphism in the VKOR gene, wherein the allele of the single nucleotide polymorphism is correlated with decreased sensitivity to warfarin, thereby identifying the subject having decreased sensitivity to warfarin;

wherein the single nucleotide polymorphism in the VKOR gene is a G>A alteration at the position corresponding to nucleotide 4769 of SEQ ID NO:11.

2. The method of claim 1, wherein said detecting comprises sequencing the VKOR gene at the position corresponding to nucleotide 4769 of SEQ ID NO:11.

3. The method of claim 1, wherein said detecting comprises performing a hybridization assay.

4. The method of claim 1, wherein said detecting comprises performing a nucleic acid amplification assay.

5. A method of determining a suitable dose of warfarin for a human subject, comprising detecting in the subject the presence of an allele of a single nucleotide polymorphism in the VKOR gene, wherein the allele of the single nucleotide polymorphism is correlated with decreased sensitivity to warfarin; and identifying a suitable dose of warfarin for the subject based on said determining;

wherein the single nucleotide polymorphism in the VKOR gene is a G>A alteration at the position corresponding to nucleotide 4769 of SEQ ID NO:11.

6. The method of claim 5, further comprising administering warfarin to the subject at a dosage determined from said identifying.

7. The method of claim 5, wherein said detecting comprises sequencing the VKOR gene at the position corresponding to nucleotide 4769 of SEQ ID NO:11.

8. The method of claim 5, wherein said detecting comprises performing a hybridization assay.

9. The method of claim 5, wherein said detecting comprises performing a nucleic acid amplification assay.

10. A method of identifying a human subject having decreased sensitivity to warfarin, comprising:

a) correlating the presence of an allele of a single nucleotide polymorphism in the VKOR gene with decreased sensitivity to warfarin; and b) detecting the allele of the single nucleotide polymorphism of step (a) in the subject, thereby identifying the subject as having decreased sensitivity to warfarin, wherein the allele of the single nucleotide polymorphism in the VKOR gene is a G>A alteration at the position corresponding to nucleotide 4769 of SEQ ID NO:11.

11. The method of claim 10, wherein said detecting comprises sequencing the VKOR gene at the position corresponding to nucleotide 4769 of SEQ ID NO:11.

12. The method of claim 10, wherein said detecting comprises performing a hybridization assay.

13. The method of claim 10, wherein said detecting comprises performing a nucleic acid amplification assay.

14. A method of amplifying a segment of a VKOR genomic nucleotide sequence, comprising:

a) choosing a first oligonucleotide primer from the 3' end of a nucleic acid molecule comprising the nucleotide sequence of SEQ ID NO:8;

b) choosing a second oligonucleotide primer from the 5' end of a nucleic acid molecule comprising the nucleotide sequence of SEQ ID NO: 8;

c) adding said first primer and said second primer to a nucleic acid sample; and d) amplifying a segment of the VKOR genomic nucleotide sequence defined by the first primer and the second primer, wherein the amplified segment comprises an allele of a single nucleotide polymorphism that is correlated with decreased sensitivity to warfarin, wherein the allele of the single nucleotide polymorphism in the VKOR gene is a G>A alteration at the position corresponding to nucleotide 4769 of SEQ ID NO: 11, and wherein said nucleic acid sample is from a subject in need of warfarin therapy.

15. A method of amplifying a segment of a VKOR genomic nucleotide sequence, comprising:

a) choosing a first oligonucleotide primer from a nucleic acid molecule comprising the nucleotide sequence of SEQ ID NO:8;

b) choosing a second oligonucleotide primer from a nucleic acid molecule comprising the nucleotide sequence of SEQ ID NO:8 that differs in nucleotide sequence from the first oligonucleotide primer;

c) adding said first primer and said second primer to a nucleic acid sample; and d) amplifying a segment of the VKOR genomic nucleotide sequence defined by the first primer and the second primer, wherein the amplified segment comprises an allele of a single nucleotide polymorphism that is correlated with decreased sensitivity to warfarin, wherein the allele of the single nucleotide polymorphism in the VKOR gene is a G>A alteration at the position corresponding to nucleotide 4769 of SEQ ID NO: 11, and wherein said nucleic acid sample is from a subject in need of warfarin therapy.

* * * * *

UNITED STATES PATENT AND TRADEMARK OFFICE

CERTIFICATE OF CORRECTION

PATENT NO. : 7,858,318 B2
APPLICATION NO. : 12/361053
DATED : December 28, 2010
INVENTOR(S) : Stafford et al.

It is certified that error appears in the above-identified patent and that said Letters Patent is hereby corrected as shown below:

On the Title Page:

Item (56) References Cited, Page 2, Other Publications, Right Column,

"Bogousslavsky et al.", Line 32: Please correct "Bogousslaysky et al." to read -- Bogousslavsky et al. --

"Bogousslavsky et al.", Line 33; Please correct "*Scand.* 77:464-471" to read -- *Scand.* 71:464-471 --

References Cited, Page 6, Other Publications, Left Column,

"Wasley et al.", Line 65: Please correct "Wesley et al." to read -- Wasley et al. --

Signed and Sealed this
Fifth Day of July, 2011

David J. Kappos
*Director of the United States Patent and Trademark Office*

SEQUENCE LISTING

<160> NUMBER OF SEQ ID NOS: 34

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 1
tccaacagca tattcggttg c 21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 2
ttcttggacc ttccggaaac t 21

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 3
gaaggtgaag gtcggagtc 19

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 4
gaagatggtg atgggatttc 20

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 5
ctaggtgagg ccaagaagca a 21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 6
ctgttcctct cagcagactg c 21

<210> SEQ ID NO 7
<211> LENGTH: 12
<212> TYPE: PRT
<213> ORGANISM: Artificial sequence
<220> FEATURE:
<223> OTHER INFORMATION: HPC4 tag sequence

<400> SEQUENCE: 7

Glu Asp Gln Val Asp Pro Arg Leu Ile Asp Gly Lys
1 5 10

<210> SEQ ID NO 8
<211> LENGTH: 3915
<212> TYPE: DNA
<213> ORGANISM: Homo sapiens

<400> SEQUENCE: 8
ggttttctcc gcgggcgcct cgggcggaac ctggagataa tgggcagcac ctgggggagc 60
cctggctggg tgcggctcgc tctttgcctg acgggcttag tgctctcgct ctacgcgctg 120
cacgtgaagg cggcgcgcgc ccgggaccgg gattaccgcg cgctctgcga cgtgggcacc 180
gccatcagct gttcgcgcgt cttctcctcc aggtgtgcac gggagtggga ggcgtggggc 240

-continued

```
ctcggagcag ggcggccagg atgccagatg attattctgg agtctgggat cggtgtgccc    300
ggggaacgga cacggggctg gactgctcgc ggggtcgttg cacaggggct gagctaccca    360
gcgatactgg tgttcgaaat aagagtgcga ggcaagggac cagacagtgc tggggactgg    420
gattattccg gggactcgca cgtgaattgg atgccaagga ataacggtga ccaggaaagg    480
cggggaggca ggatggcggt agagattgac gatggtctca aggacggcgc gcaggtgaag    540
gggggtgttg gcgatggctg cgcccaggaa caaggtggcc cggtctggct gtgcgtgatg    600
gccaggcgtt agcataatga cggaatacag aggaggcgag tgagtggcca gggagctgga    660
gattctgggg tccagggcaa agataatctg cccccgactc ccagtctctg atgcaaaacc    720
gagtgaaccg ttataccagc cttgccattt taagaattac ttaagggccg ggcgcggtgg    780
cccactcctg taatcccagc actttgggag gccgaggcgg atggatcact tgaagtcagg    840
agttgaccag cctggccaac atggtgaaag cctgtctcta ccaaaaatag aaaaattaat    900
cgggcgctat ggcgggtgcc ttaatcccag ctactcgggg ggctaaggc aggagaatcg    960
cttgaacccg ggaggcggag gtttcagtga gccgagatcg cgccactgca ctccagcctg   1020
ggccagagtg agactccgtc tcaaaaaaaa aaaaaaaaaa aaaaaaaaag agacttactt   1080
aaggtctaag atgaaaagca gggcctacgg agtagccacg tccgggcctg gtctggggag   1140
aggggaggat agggtcagtg acatggaatc ctgacgtggc caaaggtgcc cggtgccagg   1200
agatcatcga cccttggact aggatgggag gtcggggaac agaggatagc ccaggtggct   1260
tcttggaaat cacctttctc gggcagggtc caaggcactg ggttgacagt cctaacctgg   1320
ttccacccca ccccacccct ctgccaggtg gggcaggggt ttcgggctgg tggagcatgt   1380
gctgggacag gacagcatcc tcaatcaatc caacagcata ttcggttgca tcttctacac   1440
actacagcta ttgttaggtg agtggctccg ccccctccct gcccgccccg ccccgcccct   1500
catccccctt ggtcagctca gccccactcc atgcaatctt ggtgatccac acagctgaca   1560
gccagctagc tgctcatcac ggagcgtcct gcgggtgggg atgtggggag gtaactaaca   1620
ggagtctttt aattggttta agtactgtta gaggctgaag ggcccttaaa gacatcctag   1680
gtccccaggt tttttgtttg ttgttgtttt gagacagggt ctggctctgt tgcccaaagt   1740
gaggtctagg atgcccttag tgtgcactgg cgtgatctca gttcatggca acctctgcct   1800
ccctgcccaa gggatcctcc caccttagcc tcccaagcag ctggaatcac aggcgtgcac   1860
cactatgccc agctaatttt tgtttttgtt tttttttggt agagatggtg tctcgccatg   1920
ttgcccaggc tggtctcaag caatctgtct gcctcagcct cccaaagtgc tggggggatt   1980
acaggcgtga gctaccatgc cccaccaaca ccccagtttt gtggaaaaga tgccgaaatt   2040
cctttttaag gagaagctga gcatgagcta tcttttgtct catttagtgc tcagcaggaa   2100
aatttgtatc tagtcccata agaacagaga gaggaaccaa gggagtggaa gacgatggcg   2160
ccccaggcct tgctgatgcc atatgccgga gatgagacta tccattacca cccttcccag   2220
caggctccca cgctcccttt gagtcaccct tcccagctcc agagaaggca tcactgaggg   2280
aggcccagca ccatggtcct ggctgacaca tggttcagac ttggccgatt tatttaagaa   2340
attttattgc tcagaacttt ccctccctgg gcaatggcaa gagcttcaga gaccagtccc   2400
ttggagggga cctgttgaag ccttcttttt tttttttttt aagaaataat cttgctctgt   2460
tgcccaggct ggagtgcagt ggcacaatca tagctcactg taacctggct caagcgatcc   2520
tcctgagtag ctaggactat aggcatgtca ctgcacccag ctaatttttt tttttttttt   2580
tttttttttt ttgcgacata gtctcgctct gtcaccaggc tggagtgcag tggcacgatc   2640
```

-continued

```
ttggctcact gcaacctctg cctcccgggt tcaagcaatt ttcctgcctc agcctcctga   2700

gtagctggga ctacaggcgc gtgtcaccac gcccagctaa tttttgtatt tttagtggag   2760

acagggtttc accatgttgg ctaggatggt ctcaatctct tgacctggtg atccatccgc   2820

cttggcctcc caaagtgcta ggattacagg cgtgagtcaa cctcaccggg cattttttt    2880

ttgagacgaa gtcttgctct tgctgcccaa gctggaatgt ggtggcatga tctcggctca   2940

ctgcaacctc cacctcctag gttcaagcga ttctccacct tagcctcccc agcagctggg   3000

attacaggtg cccatcaaca cacccggcta atttttgtat ttttattaga gatggggttt   3060

tgccatgttg gccaggctgc tctcgaactc ctaacctcag gtgatccacc cccattggcc   3120

tcccaaaata ctgggattac aggcatgagc caccgtgccc agctgaattt ctaaattttt   3180

gatagagatc gggtctttct atgttgccca agctggtctt gaactcctag cctaaagcag   3240

tcttcccacc tcggcctccc agagtgtttg gaatacgtgc gtaagccacc acatctgccc   3300

tggagcctct tgttttagag acccttccca gcagctcctg gcatctaggt agtgcagtga   3360

catcatggag tgttcgggag gtggccagtg cctgaagccc acaccggacc ctcttctgcc   3420

ttgcaggttg cctgcggaca cgctgggcct ctgtcctgat gctgctgagc tccctggtgt   3480

ctctcgctgg ttctgtctac ctggcctgga tcctgttctt cgtgctctat gatttctgca   3540

ttgtttgtat caccacctat gctatcaacg tgagcctgat gtggctcagt ttccggaagg   3600

tccaagaacc ccagggcaag gctaagaggc actgagccct caacccaagc caggctgacc   3660

tcatctgctt tgctttggca tgtgagcctt gcctaagggg gcatatctgg gtccctagaa   3720

ggccctagat gtggggcttc tagattaccc cctcctcctg ccatacccgc acatgacaat   3780

ggaccaaatg tgccacacgc tcgctctttt ttacacccag tgcctctgac tctgtcccca   3840

tgggctggtc tccaaagctc tttccattgc ccagggaggg aaggttctga gcaataaagt   3900

ttcttagatc aatca                                                    3915


<210> SEQ ID NO 9
<211> LENGTH: 806
<212> TYPE: DNA
<213> ORGANISM: Homo sapiens
<220> FEATURE:
<221> NAME/KEY: CDS
<222> LOCATION: (48)..(536)

<400> SEQUENCE: 9

ggcacgaggg ttttctccgc gggcgcctcg ggcggaacct ggagata atg ggc agc       56
                                                    Met Gly Ser
                                                    1

acc tgg ggg agc cct ggc tgg gtg cgg ctc gct ctt tgc ctg acg ggc      104
Thr Trp Gly Ser Pro Gly Trp Val Arg Leu Ala Leu Cys Leu Thr Gly
    5                   10                  15

tta gtg ctc tcg ctc tac gcg ctg cac gtg aag gcg gcg cgc gcc cgg      152
Leu Val Leu Ser Leu Tyr Ala Leu His Val Lys Ala Ala Arg Ala Arg
20                  25                  30                  35

gac cgg gat tac cgc gcg ctc tgc gac gtg ggc acc gcc atc agc tgt      200
Asp Arg Asp Tyr Arg Ala Leu Cys Asp Val Gly Thr Ala Ile Ser Cys
                40                  45                  50

tcg cgc gtc ttc tcc tcc agg tgg ggc agg ggt ttc ggg ctg gtg gag      248
Ser Arg Val Phe Ser Ser Arg Trp Gly Arg Gly Phe Gly Leu Val Glu
            55                  60                  65

cat gtg ctg gga cag gac agc atc ctc aat caa tcc aac agc ata ttc      296
His Val Leu Gly Gln Asp Ser Ile Leu Asn Gln Ser Asn Ser Ile Phe
        70                  75                  80
```

```
ggt tgc atc ttc tac aca cta cag cta ttg tta ggt tgc ctg cgg aca      344
Gly Cys Ile Phe Tyr Thr Leu Gln Leu Leu Leu Gly Cys Leu Arg Thr
    85                  90                  95

cgc tgg gcc tct gtc ctg atg ctg ctg agc tcc ctg gtg tct ctc gct      392
Arg Trp Ala Ser Val Leu Met Leu Leu Ser Ser Leu Val Ser Leu Ala
100                 105                 110                 115

ggt tct gtc tac ctg gcc tgg atc ctg ttc ttc gtg ctc tat gat ttc      440
Gly Ser Val Tyr Leu Ala Trp Ile Leu Phe Phe Val Leu Tyr Asp Phe
                120                 125                 130

tgc att gtt tgt atc acc acc tat gct atc aac gtg agc ctg atg tgg      488
Cys Ile Val Cys Ile Thr Thr Tyr Ala Ile Asn Val Ser Leu Met Trp
            135                 140                 145

ctc agt ttc cgg aag gtc caa gaa ccc cag ggc aag gct aag agg cac      536
Leu Ser Phe Arg Lys Val Gln Glu Pro Gln Gly Lys Ala Lys Arg His
        150                 155                 160

tgagccctca acccaagcca ggctgacctc atctgctttg ctttggcatg tgagccttgc    596

ctaagggggc atatctgggt ccctagaagg ccctagatgt ggggcttcta gattaccccc    656

tcctcctgcc atacccgcac atgacaatgg accaaatgtg ccacacgctc gctctttttt    716

acacccagtg cctctgactc tgtccccatg ggctggtctc caaagctctt tccattgccc    776

agggagggaa ggttctgagc aataaagttt                                      806


<210> SEQ ID NO 10
<211> LENGTH: 163
<212> TYPE: PRT
<213> ORGANISM: Homo sapiens

<400> SEQUENCE: 10

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
        115                 120                 125

Tyr Asp Phe Cys Ile Val Cys Ile Thr Thr Tyr Ala Ile Asn Val Ser
    130                 135                 140

Leu Met Trp Leu Ser Phe Arg Lys Val Gln Glu Pro Gln Gly Lys Ala
145                 150                 155                 160

Lys Arg His


<210> SEQ ID NO 11
<211> LENGTH: 5915
<212> TYPE: DNA
<213> ORGANISM: Homo sapiens

<400> SEQUENCE: 11
```

-continued

```
caccatcaga tgggacgtct gtgaaggaga gacctcatct ggcccacagc ttggaaagga     60

gagactgact gttgagttga tgcaagctca ggtgttgcca ggcgggcgcc atgatagtag    120

agaggttagg atactgtcaa gggtgtgtgt ggccaaagga gtggttctgt gaatgtatgg    180

gagaaaggga gaccgaccac caggaagcac tggtgaggca ggacccggga ggatgggagg    240

ctgcagcccg aatggtgcct gaaatagttt caggggaaat gcttggttcc cgaatcggat    300

cgccgtattc gctggatccc ctgatccgct ggtctctagg tcccggatgc tgcaattctt    360

acaacaggac ttggcatagg gtaagcgcaa atgctgttaa ccacactaac acactttttt    420

ttttcttttt tttttttgag acagagtctc actctgtcgg cctggctgga gtgcagtggc    480

acgatctcgg ctcactgcaa cctccggctc cccggctcaa gcaattctcc tgcctcagcc    540

tcccgagtag ctgggattac aggcatgtgc caccacgccc ggctaatttt tgtattttta    600

gttgagatgg ggtttcacca tgttggcgag gctggtcttg aactcctgac ctcaggtaat    660

ccgccagcct cggcctccca aagtgctggg attacaagcg tgagccaccg tgcccggcca    720

acagttttta aatctgtgga gacttcattt cccttgatgc cttgcagccg cgccgactac    780

aactcccatc atgcctggca gccgctgggg ccgcgattcc gcacgtccct tacccgcttc    840

actagtcccg gcattcttcg ctgttttcct aactcgcccg cttgactagc gccctggaac    900

agccatttgg gtcgtggagt gcgagcacgg ccggccaatc gccgagtcag agggccagga    960

ggggcgcggc cattcgccgc ccggccccctg ctccgtggct ggttttctcc gcgggcgcct   1020

cgggcggaac ctggagataa tgggcagcac ctgggggagc cctggctggg tgcggctcgc   1080

tctttgcctg acgggcttag tgctctcgct ctacgcgctg cacgtgaagg cggcgcgcgc   1140

ccgggaccgg gattaccgcg cgctctgcga cgtgggcacc gccatcagct gttcgcgcgt   1200

cttctcctcc aggtgtgcac gggagtggga ggcgtggggc ctcggagcag ggcggccagg   1260

atgccagatg attattctgg agtctgggat cggtgtgccc ggggaacgga cacggggctg   1320

gactgctcgc ggggtcgttg cacaggggct gagctaccca gcgatactgg tgttcgaaat   1380

aagagtgcga ggcaagggac cagacagtgc tggggactgg gattattccg gggactcgca   1440

cgtgaattgg atgccaagga ataacggtga ccaggaaagg cggggaggca ggatggcggt   1500

agagattgac gatggtctca aggacggcgc gcaggtgaag gggggtgttg gcgatggctg   1560

cgcccaggaa caaggtggcc cggtctggct gtgcgtgatg gccaggcgtt agcataatga   1620

cggaatacag aggaggcgag tgagtggcca gggagctgga gattctgggg tccagggcaa   1680

agataatctg cccccgactc ccagtctctg atgcaaaacc gagtgaaccg ttataccagc   1740

cttgccattt taagaattac ttaagggccg ggcgcggtgg cccactcctg taatcccagc   1800

actttgggag gccgaggcgg atggatcact tgaagtcagg agttgaccag cctggccaac   1860

atggtgaaag cctgtctcta ccaaaaatag aaaaattaat cgggcgctat ggcgggtgcc   1920

ttaatcccag ctactcgggg gggctaaggc aggagaatcg cttgaacccg ggaggcggag   1980

gtttcagtga gccgagatcg cgccactgca ctccagcctg ggccagagtg agactccgtc   2040

tcaaaaaaaa aaaaaaaaaa aaaaaaaaag agacttactt aaggtctaag atgaaaagca   2100

gggcctacgg agtagccacg tccgggcctg gtctggggag aggggaggat agggtcagtg   2160

acatggaatc ctgacgtggc caaaggtgcc cggtgccagg agatcatcga cccttggact   2220

aggatgggag gtcggggaac agaggatagc ccaggtggct tcttggaaat cacctttctc   2280

gggcagggtc caaggcactg ggttgacagt cctaacctgg ttccacccca ccccacccct   2340

ctgccaggtg gggcaggggt ttcgggctgg tggagcatgt gctgggacag gacagcatcc   2400
```

-continued

```
tcaatcaatc caacagcata ttcggttgca tcttctacac actacagcta ttgttaggtg   2460
agtggctccg ccccctccct gcccgccccg ccccgcccct catcccccctt ggtcagctca   2520
gccccactcc atgcaatctt ggtgatccac acagctgaca gccagctagc tgctcatcac   2580
ggagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
caccttagcc tcccaagcag ctggaatcac aggcgtgcac cactatgccc agctaatttt   2880
tgtttttgtt tttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt ccttttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccatggtcct   3300
ggctgacaca tggttcagac ttggccgatt tatttaagaa attttattgc tcagaacttt   3360
ccctccctgg gcaatggcaa gagcttcaga gaccagtccc ttggaggggga cctgttgaag   3420
ccttcttttt tttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ctggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
tgtgagcctt gcctaagggg gcatatctgg gtccctagaa ggccctagat gtggggcttc   4740
```

-continued

```
tagattaccc cctcctcctg ccatacccgc acatgacaat ggaccaaatg tgccacacgc    4800

tcgctctttt ttacacccag tgcctctgac tctgtcccca tgggctggtc tccaaagctc    4860

tttccattgc ccagggaggg aaggttctga gcaataaagt ttcttagatc aatcagccaa    4920

gtctgaacca tgtgtctgcc atggactgtg gtgctgggcc tccctcggtg ttgccttctc    4980

tggagctggg aagggtgagt cagagggaga gtggagggcc tgctgggaag ggtggttatg    5040

ggtagtctca tctccagtgt gtggagtcag caaggcctgg ggcaccattg gcccccaccc    5100

ccaggaaaca ggctggcagc tcgctcctgc tgcccacagg agccaggcct cctctcctgg    5160

gaaggctgag cacacacctg gaagggcagg ctgcccttct ggttctgtaa atgcttgctg    5220

ggaagttctt ccttgagttt aactttaacc cctccagttg ccttatcgac cattccaagc    5280

cagtattggt agccttggag ggtcagggcc aggttgtgaa ggtttttgtt ttgcctatta    5340

tgccctgacc acttacctac atgccaagca ctgtttaaga acttgtgttg gcagggtgca    5400

gtggctcaca cctgtaatcc ctgtactttg ggaggccaag gcaggaggat cacttgaggc    5460

caggagttcc agaccagcct gggcaaaata gtgagacccc tgtctctaca aaaaaaaaaa    5520

aaaaaaaaaa ttagccaggc atggtggtgt atgtacctat agtcccaact aatcgggaag    5580

ctggcgggaa gactgcttga gcccagaagg ttgaggctgc agtgagccat gatcactgca    5640

ctccagcctg agcaacagag caagaccgtc tccaaaaaaa aacaaaaaac aaaaaaaaac    5700

ttgtgttaac gtgttaaact cgtttaatct ttacagtgat ttatgaggtg ggtactatta    5760

ttatccctat cttgatgata gggacagagt ggctaattag tatgcctgag atcacacagc    5820

tactgcagga ggctctcagg atttgaatcc acctggtcca tctggctcca gcatctatat    5880

gctttttttt ttgttggttt gtttttgaga cggac                               5915
```

<210> SEQ ID NO 12
<211> LENGTH: 5915
<212> TYPE: DNA
<213> ORGANISM: Homo sapiens

<400> SEQUENCE: 12

```
caccatcaga tgggacgtct gtgaaggaga gacctcatct ggcccacagc ttggaaagga      60

gagactgact gttgagttga tgcaagctca ggtgttgcca ggcgggcgcc atgatagtag     120

agaggttagg atactgtcaa gggtgtgtgt ggccaaagga gtggttctgt gaatgtatgg     180

gagaaaggga gaccgaccac caggaagcac tggtgaggca ggacccggga ggatgggagg     240

ctgcagcccg aatggtgcct gaaatagttt caggggaaat gcttggttcc cgaatcggat     300

cgccgtattc gctggatccc ctgatccgct ggtctctagg tcccggatgc tgcaattctt     360

acaacaggac ttggcatagg gtaagcgcaa atgctgttaa ccacactaac acactttttt     420

ttttcttttt tttttttgag acagagtctc actctgtcgg cctggctgga gtgcagtggc     480

acgatctcgg ctcactgcaa cctccggctc cccggctcaa gcaattctcc tgcctcagcc     540

tcccgagtag ctgggattac aggcatgtgc caccacgccc ggctaatttt tgtattttta     600

gttgagatgg ggtttcacca tgttggcgag gctggtcttg aactcctgac ctcaggtaat     660

ccgccagcct cggcctccca aagtgctggg attacaagcg tgagccaccg tgcccggcca     720

acagttttta aatctgtgga gacttcattt cccttgatgc cttgcagccg cgccgactac     780

aactcccatc atgcctggca gccgctgggg ccgcgattcc gcacgtccct tacccgcttc     840

actagtcccg gcattcttcg ctgttttcct aactcgcccg cttgactagc gccctggaac     900

agccatttgg gtcgtggagt gcgagcacgg ccggccaatc gccgagtcag agggccagga     960
```

-continued

```
ggggcgcggc cattcgccgc ccggcccctg ctccgtggct ggttttctcc gcgggcgcct   1020
cgggcggaac ctggagataa tgggcagcac ctgggggagc cctggctggg tgcggctcgc   1080
tctttgcctg acgggcttag tgctctcgct ctacgcgctg cacgtgaagg cggcgcgcgc   1140
ccgggaccgg gattaccgcg cgctctgcga cgtgggcacc gccatcagct gttcgcgcgt   1200
cttctcctcc aggtgtgcac gggagtggga ggcgtggggc ctcggagcag ggcggccagg   1260
atgccagatg attattctgg agtctgggat cggtgtgccc ggggaacgga cacggggctg   1320
gactgctcgc ggggtcgttg cacaggggct gagctaccca gcgatactgg tgttcgaaat   1380
aagagtgcga ggcaagggac cagacagtgc tggggactgg gattattccg gggactcgca   1440
cgtgaattgg atgccaagga ataacggtga ccaggaaagg cggggaggca ggatggcggt   1500
agagattgac gatggtctca aggacggcgc gcaggtgaag gggggtgttg gcgatggctg   1560
cgcccaggaa caaggtggcc cggtctggct gtgcgtgatg gccaggcgtt agcataatga   1620
cggaatacag aggaggcgag tgagtggcca gggagctgga gattctgggg tccagggcaa   1680
agataatctg cccccgactc ccagtctctg atgcaaaacc gagtgaaccg ttataccagc   1740
cttgccattt taagaattac ttaagggccg ggcgcggtgg cccactcctg taatcccagc   1800
actttgggag gccgaggcgg atggatcact tgaagtcagg agttgaccag cctggccaac   1860
atggtgaaag cctgtctcta ccaaaaatag aaaaattaat cgggcgctat ggcgggtgcc   1920
ttaatcccag ctactcgggg gggctaaggc aggagaatcg cttgaacccg ggaggcggag   1980
gtttcagtga gccgagatcg cgccactgca ctccagcctg ggccagagtg agactccgtc   2040
tcaaaaaaaa aaaaaaaaaa aaaaaaaaag agacttactt aaggtctaag atgaaaagca   2100
gggcctacgg agtagccacg tccgggcctg gtctggggag aggggaggat agggtcagtg   2160
acatggaatc ctgacgtggc caaaggtgcc cggtgccagg agatcatcga cccttggact   2220
aggatgggag gtcggggaac agaggatagc ccaggtggct tcttggaaat cacctttctc   2280
gggcagggtc caaggcactg ggttgacagt cctaacctgg ttccacccca ccccacccct   2340
ctgccaggtg gggcaggggt ttcgggctgg tggagcatgt gctgggacag gacagcatcc   2400
tcaatcaatc caacagcata ttcggttgca tcttctacac actacagcta ttgttaggtg   2460
agtggctccg ccccctccct gcccgccccg ccccgcccct catccccctt ggtcagctca   2520
gccccactcc atgcaatctt ggtgatccac acagctgaca gccagctagc tgctcatcac   2580
cgagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
caccttagcc tcccaagcag ctggaatcac aggcgtgcac cactatgccc agctaatttt   2880
tgtttttgtt ttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt cctttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccatggtcct   3300
```

-continued

```
ggctgacaca tggttcagac ttggccgatt tatttaagaa attttattgc tcagaacttt   3360
ccctccctgg gcaatggcaa gagcttcaga gaccagtccc ttggagggga cctgttgaag   3420
ccttcttttt tttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ctggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
tgtgagcctt gcctaagggg gcatatctgg gtccctagaa ggccctagat gtggggcttc   4740
tagattaccc cctcctcctg ccatacccgc acatgacaat ggaccaaatg tgccacacgc   4800
tcgctctttt ttacacccag tgcctctgac tctgtcccca tgggctggtc tccaaagctc   4860
tttccattgc ccagggaggg aaggttctga gcaataaagt ttcttagatc aatcagccaa   4920
gtctgaacca tgtgtctgcc atggactgtg gtgctgggcc tccctcggtg ttgccttctc   4980
tggagctggg aagggtgagt cagagggaga gtggagggcc tgctgggaag ggtggttatg   5040
ggtagtctca tctccagtgt gtggagtcag caaggcctgg ggcaccattg gcccccaccc   5100
ccaggaaaca ggctggcagc tcgctcctgc tgcccacagg agccaggcct cctctcctgg   5160
gaaggctgag cacacacctg gaagggcagg ctgcccttct ggttctgtaa atgcttgctg   5220
ggaagttctt ccttgagttt aactttaacc cctccagttg ccttatcgac cattccaagc   5280
cagtattggt agccttggag ggtcagggcc aggttgtgaa ggtttttgtt ttgcctatta   5340
tgccctgacc acttacctac atgccaagca ctgtttaaga acttgtgttg gcagggtgca   5400
gtggctcaca cctgtaatcc ctgtactttg ggaggccaag gcaggaggat cacttgaggc   5460
caggagttcc agaccagcct gggcaaaata gtgagacccc tgtctctaca aaaaaaaaaa   5520
aaaaaaaaaa ttagccaggc atggtggtgt atgtacctat agtcccaact aatcgggaag   5580
ctggcgggaa gactgcttga gcccagaagg ttgaggctgc agtgagccat gatcactgca   5640
ctccagcctg agcaacagag caagaccgtc tccaaaaaaa aacaaaaaac aaaaaaaaac   5700
```

-continued

```
ttgtgttaac gtgttaaact cgtttaatct ttacagtgat ttatgaggtg ggtactatta   5760

ttatccctat cttgatgata gggacagagt ggctaattag tatgcctgag atcacacagc   5820

tactgcagga ggctctcagg atttgaatcc acctggtcca tctggctcca gcatctatat   5880

gctttttttt ttgttggttt gtttttgaga cggac                               5915
```

<210> SEQ ID NO 13
<211> LENGTH: 5915
<212> TYPE: DNA
<213> ORGANISM: Homo sapiens

<400> SEQUENCE: 13

```
caccatcaga tgggacgtct gtgaaggaga gacctcatct ggcccacagc ttggaaagga     60

gagactgact gttgagttga tgcaagctca ggtgttgcca ggcgggcgcc atgatagtag    120

agaggttagg atactgtcaa gggtgtgtgt ggccaaagga gtggttctgt gaatgtatgg    180

gagaaaggga gaccgaccac caggaagcac tggtgaggca ggacccggga ggatgggagg    240

ctgcagcccg aatggtgcct gaaatagttt caggggaaat gcttggttcc cgaatcggat    300

cgccgtattc gctggatccc ctgatccgct ggtctctagg tcccggatgc tgcaattctt    360

acaacaggac ttggcatagg gtaagcgcaa atgctgttaa ccacactaac acactttttt    420

ttttcttttt tttttttgag acagagtctc actctgtcgg cctggctgga gtgcagtggc    480

acgatctcgg ctcactgcaa cctccggctc cccggctcaa gcaattctcc tgcctcagcc    540

tcccgagtag ctgggattac aggcatgtgc caccacgccc ggctaatttt tgtattttta    600

gttgagatgg ggtttcacca tgttggcgag gctggtcttg aactcctgac ctcaggtaat    660

ccgccagcct cggcctccca aagtgctggg attacaagcg tgagccaccg tgcccggcca    720

acagttttta aatctgtgga gacttcattt cccttgatgc cttgcagccg cgccgactac    780

aactcccatc atgcctggca gccgctgggg ccgcgattcc gcacgtccct tacccgcttc    840

actagtcccg gcattcttcg ctgttttcct aactcgcccg cttgactagc gccctggaac    900

agccatttgg gtcgtggagt gcgagcacgg ccggccaatc gccgagtcag agggccagga    960

ggggcgcggc cattcgccgc ccggcccctg ctccgtggct ggttttctcc gcgggcgcct   1020

cgggcggaac ctggagataa tgggcagcac ctgggggagc cctggctggg tgcggctcgc   1080

tctttgcctg acgggcttag tgctctcgct ctacgcgctg cacgtgaagg cggcgcgcgc   1140

ccgggaccgg gattaccgcg cgctctgcga cgtgggcacc gccatcagct gttcgcgcgt   1200

cttctcctcc aggtgtgcac gggagtggga ggcgtggggc ctcggagcag ggcggccagg   1260

atgccagatg attattctgg agtctgggat cggtgtgccc ggggaacgga cacggggctg   1320

gactgctcgc ggggtcgttg cacaggggct gagctaccca gcgatactgg tgttcgaaat   1380

aagagtgcga ggcaagggac cagacagtgc tggggactgg gattattccg gggactcgca   1440

cgtgaattgg atgccaagga ataacggtga ccaggaaagg cggggaggca ggatggcggt   1500

agagattgac gatggtctca aggacggcgc gcaggtgaag gggggtgttg gcgatggctg   1560

cgcccaggaa caaggtggcc cggtctggct gtgcgtgatg gccaggcgtt agcataatga   1620

cggaatacag aggaggcgag tgagtggcca gggagctgga gattctgggg tccagggcaa   1680

agataatctg cccccgactc ccagtctctg atgcaaaacc gagtgaaccg ttataccagc   1740

cttgccattt taagaattac ttaagggccg ggcgcggtgg cccactcctg taatcccagc   1800

actttgggag gccgaggcgg atggatcact tgaagtcagg agttgaccag cctggccaac   1860
```

-continued

```
atggtgaaag cctgtctcta ccaaaaatag aaaaattaat cgggcgctat ggcgggtgcc   1920
ttaatcccag ctactcgggg gggctaaggc aggagaatcg cttgaacccg ggaggcggag   1980
gtttcagtga gccgagatcg cgccactgca ctccagcctg ggccagagtg agactccgtc   2040
tcaaaaaaaa aaaaaaaaaa aaaaaaaaag agacttactt aaggtctaag atgaaaagca   2100
gggcctacgg agtagccacg tccgggcctg gtctggggag aggggaggat agggtcagtg   2160
acatggaatc ctgacgtggc caaaggtgcc cggtgccagg agatcatcga cccttggact   2220
aggatgggag gtcggggaac agaggatagc ccaggtggct tcttggaaat cacctttctc   2280
gggcagggtc caaggcactg ggttgacagt cctaacctgg ttccacccca ccccacccct   2340
ctgccaggtg gggcaggggt ttcgggctgg tggagcatgt gctgggacag gacagcatcc   2400
tcaatcaatc caacagcata ttcggttgca tcttctacac actacagcta ttgttaggtg   2460
agtggctccg ccccctccct gcccgccccg ccccgcccct catccccctt ggtcagctca   2520
gccccactcc atgcaatctt ggtgatccac acagctgaca gccagctagc tgctcatcac   2580
ggagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
caccttagcc tcccaagcag ctggaatcac aggcgtgcac cactatgccc agctaatttt   2880
tgtttttgtt ttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt cctttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccacggtcct   3300
ggctgacaca tggttcagac ttggccgatt tatttaagaa attttattgc tcagaacttt   3360
ccctccctgg gcaatggcaa gagcttcaga gaccagtccc ttggagggga cctgttgaag   3420
ccttcttttt ttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
```

-continued

```
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ctggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
tgtgagcctt gcctaagggg gcatatctgg gtccctagaa ggccctagat gtggggcttc   4740
tagattaccc cctcctcctg ccatacccgc acatgacaat ggaccaaatg tgccacacgc   4800
tcgctctttt ttacacccag tgcctctgac tctgtcccca tgggctggtc tccaaagctc   4860
tttccattgc ccagggaggg aaggttctga gcaataaagt ttcttagatc aatcagccaa   4920
gtctgaacca tgtgtctgcc atggactgtg gtgctgggcc tccctcggtg ttgccttctc   4980
tggagctggg aagggtgagt cagagggaga gtggagggcc tgctgggaag ggtggttatg   5040
ggtagtctca tctccagtgt gtggagtcag caaggcctgg ggcaccattg gcccccaccc   5100
ccaggaaaca ggctggcagc tcgctcctgc tgcccacagg agccaggcct cctctcctgg   5160
gaaggctgag cacacacctg gaagggcagg ctgcccttct ggttctgtaa atgcttgctg   5220
ggaagttctt ccttgagttt aactttaacc cctccagttg ccttatcgac cattccaagc   5280
cagtattggt agccttggag ggtcagggcc aggttgtgaa ggtttttgtt ttgcctatta   5340
tgccctgacc acttacctac atgccaagca ctgtttaaga acttgtgttg gcagggtgca   5400
gtggctcaca cctgtaatcc ctgtactttg ggaggccaag gcaggaggat cacttgaggc   5460
caggagttcc agaccagcct gggcaaaata gtgagacccc tgtctctaca aaaaaaaaaa   5520
aaaaaaaaaa ttagccaggc atggtggtgt atgtacctat agtcccaact aatcgggaag   5580
ctggcgggaa gactgcttga gcccagaagg ttgaggctgc agtgagccat gatcactgca   5640
ctccagcctg agcaacagag caagaccgtc tccaaaaaaa aacaaaaaac aaaaaaaaac   5700
ttgtgttaac gtgttaaact cgtttaatct ttacagtgat ttatgaggtg ggtactatta   5760
ttatccctat cttgatgata gggacagagt ggctaattag tatgcctgag atcacacagc   5820
tactgcagga ggctctcagg atttgaatcc acctggtcca tctggctcca gcatctatat   5880
gcttttttt ttgttggttt gtttttgaga cggac                                5915
```

<210> SEQ ID NO 14
<211> LENGTH: 5915
<212> TYPE: DNA
<213> ORGANISM: Homo sapiens

<400> SEQUENCE: 14

```
caccatcaga tgggacgtct gtgaaggaga gacctcatct ggcccacagc ttggaaagga     60
gagactgact gttgagttga tgcaagctca ggtgttgcca ggcgggcgcc atgatagtag    120
agaggttagg atactgtcaa gggtgtgtgt ggccaaagga gtggttctgt gaatgtatgg    180
gagaaaggga gaccgaccac caggaagcac tggtgaggca ggacccggga ggatgggagg    240
ctgcagcccg aatggtgcct gaaatagttt caggggaaat gcttggttcc cgaatcggat    300
cgccgtattc gctggatccc ctgatccgct ggtctctagg tcccggatgc tgcaattctt    360
acaacaggac ttggcatagg gtaagcgcaa atgctgttaa ccacactaac acactttttt    420
```

-continued

```
ttttcttttt ttttttgag acagagtctc actctgtcgg cctggctgga gtgcagtggc     480
acgatctcgg ctcactgcaa cctccggctc cccggctcaa gcaattctcc tgcctcagcc    540
tcccgagtag ctgggattac aggcatgtgc caccacgccc ggctaatttt tgtattttta    600
gttgagatgg ggtttcacca tgttggcgag gctggtcttg aactcctgac ctcaggtaat    660
ccgccagcct cggcctccca aagtgctggg attacaagcg tgagccaccg tgcccggcca    720
acagttttta aatctgtgga gacttcattt cccttgatgc cttgcagccg cgccgactac    780
aactcccatc atgcctggca gccgctgggg ccgcgattcc gcacgtccct tacccgcttc    840
actagtcccg gcattcttcg ctgttttcct aactcgcccg cttgactagc gccctggaac    900
agccatttgg gtcgtggagt gcgagcacgg ccggccaatc gccgagtcag agggccagga    960
ggggcgcggc cattcgccgc ccggcccctg ctccgtggct ggttttctcc gcgggcgcct   1020
cgggcggaac ctggagataa tgggcagcac ctgggggagc cctggctggg tgcggctcgc   1080
tctttgcctg acgggcttag tgctctcgct ctacgcgctg cacgtgaagg cggcgcgcgc   1140
ccgggaccgg gattaccgcg cgctctgcga cgtgggcacc gccatcagct gttcgcgcgt   1200
cttctcctcc aggtgtgcac gggagtggga ggcgtggggc ctcggagcag ggcggccagg   1260
atgccagatg attattctgg agtctgggat cggtgtgccc ggggaacgga cacggggctg   1320
gactgctcgc ggggtcgttg cacaggggct gagctaccca gcgatactgg tgttcgaaat   1380
aagagtgcga ggcaagggac cagacagtgc tggggactgg gattattccg gggactcgca   1440
cgtgaattgg atgccaagga ataacggtga ccaggaaagg cggggaggca ggatggcggt   1500
agagattgac gatggtctca aggacggcgc gcaggtgaag gggggtgttg gcgatggctg   1560
cgcccaggaa caaggtggcc cggtctggct gtgcgtgatg gccaggcgtt agcataatga   1620
cggaatacag aggaggcgag tgagtggcca gggagctgga gattctgggg tccagggcaa   1680
agataatctg cccccgactc ccagtctctg atgcaaaacc gagtgaaccg ttataccagc   1740
cttgccattt taagaattac ttaagggccg ggcgcggtgg cccactcctg taatcccagc   1800
actttgggag gccgaggcgg atggatcact tgaagtcagg agttgaccag cctggccaac   1860
atggtgaaag cctgtctcta ccaaaaatag aaaaattaat cgggcgctat ggcgggtgcc   1920
ttaatcccag ctactcgggg ggctaaggc aggagaatcg cttgaacccg ggaggcggag    1980
gtttcagtga gccgagatcg cgccactgca ctccagcctg ggccagagtg agactccgtc   2040
tcaaaaaaaa aaaaaaaaaa aaaaaaaaag agacttactt aaggtctaag atgaaaagca   2100
gggcctacgg agtagccacg tccgggcctg gtctggggag aggggaggat agggtcagtg   2160
acatggaatc ctgacgtggc caaaggtgcc cggtgccagg agatcatcga cccttggact   2220
aggatgggag gtcggggaac agaggatagc ccaggtggct tcttggaaat cacctttctc   2280
gggcagggtc caaggcactg ggttgacagt cctaacctgg ttccacccca ccccacccct   2340
ctgccaggtg gggcaggggt ttcgggctgg tggagcatgt gctgggacag gacagcatcc   2400
tcaatcaatc caacagcata ttcggttgca tcttctacac actacagcta ttgttaggtg   2460
agtggctccg ccccctccct gcccgccccg ccccgcccct catccccctt ggtcagctca   2520
gccccactcc atgcaatctt ggtgatccac acagctgaca gccagctagc tgctcatcac   2580
ggagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
```

-continued

```
caccttagcc tcccaagcag ctggaatcac aggcgtgcac cactatgccc agctaatttt   2880
tgtttttgtt ttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt cctttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccatggtcct   3300
ggctgacaca tggttcagac ttggccgatt tatttaagaa attttattgc tcagaacttt   3360
ccctccctgg gcaatggcaa gagcttcaga gaccagtccc ttggagggga cctgttgaag   3420
ccttcttttt tttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ctggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
tgtgagcctt gcctaagggg gcatatctgg gtccctagaa ggccctagat gtggggcttc   4740
tagattaccc cctcctcctg ccatacccac acatgacaat ggaccaaatg tgccacacgc   4800
tcgctctttt ttacacccag tgcctctgac tctgtcccca tgggctggtc tccaaagctc   4860
tttccattgc ccagggaggg aaggttctga gcaataaagt ttcttagatc aatcagccaa   4920
gtctgaacca tgtgtctgcc atggactgtg gtgctgggcc tccctcggtg ttgccttctc   4980
tggagctggg aagggtgagt cagagggaga gtggagggcc tgctgggaag ggtggttatg   5040
ggtagtctca tctccagtgt gtggagtcag caaggcctgg ggcaccattg gcccccaccc   5100
ccaggaaaca ggctggcagc tcgctcctgc tgcccacagg agccaggcct cctctcctgg   5160
```

```
gaaggctgag cacacacctg gaagggcagg ctgcccttct ggttctgtaa atgcttgctg   5220

ggaagttctt ccttgagttt aactttaacc cctccagttg ccttatcgac cattccaagc   5280

cagtattggt agccttggag ggtcagggcc aggttgtgaa ggtttttgtt ttgcctatta   5340

tgccctgacc acttacctac atgccaagca ctgtttaaga acttgtgttg gcagggtgca   5400

gtggctcaca cctgtaatcc ctgtactttg ggaggccaag gcaggaggat cacttgaggc   5460

caggagttcc agaccagcct gggcaaaata gtgagacccc tgtctctaca aaaaaaaaaa   5520

aaaaaaaaaa ttagccaggc atggtggtgt atgtacctat agtcccaact aatcgggaag   5580

ctggcgggaa gactgcttga gcccagaagg ttgaggctgc agtgagccat gatcactgca   5640

ctccagcctg agcaacagag caagaccgtc tccaaaaaaa aacaaaaaac aaaaaaaaac   5700

ttgtgttaac gtgttaaact cgtttaatct ttacagtgat ttatgaggtg ggtactatta   5760

ttatccctat cttgatgata gggacagagt ggctaattag tatgcctgag atcacacagc   5820

tactgcagga ggctctcagg atttgaatcc acctggtcca tctggctcca gcatctatat   5880

gctttttttt ttgttggttt gtttttgaga cggac                              5915
```

<210> SEQ ID NO 15
<211> LENGTH: 5915
<212> TYPE: DNA
<213> ORGANISM: Homo sapiens

<400> SEQUENCE: 15

```
caccatcaga tgggacgtct gtgaaggaga gacctcatct ggcccacagc ttggaaagga     60

gagactgact gttgagttga tgcaagctca ggtgttgcca ggcgggcgcc atgatagtag    120

agaggttagg atactgtcaa gggtgtgtgt ggccaaagga gtggttctgt gaatgtatgg    180

gagaaaggga gaccgaccac caggaagcac tggtgaggca ggacccggga ggatgggagg    240

ctgcagcccg aatggtgcct gaaatagttt caggggaaat gcttggttcc cgaatcggat    300

cgccgtattc gctggatccc ctgatccgct ggtctctagg tcccggatgc tgcaattctt    360

acaacaggac ttggcatagg gtaagcgcaa atgctgttaa ccacactaac acactttttt    420

ttttcttttt tttttttgag acagagtctc actctgtcgg cctggctgga gtgcagtggc    480

acgatctcgg ctcactgcaa cctccggctc cccggctcaa gcaattctcc tgcctcagcc    540

tcccgagtag ctgggattac agacatgtgc caccacgccc ggctaatttt tgtattttta    600

gttgagatgg ggtttcacca tgttggcgag gctggtcttg aactcctgac ctcaggtaat    660

ccgccagcct cggcctccca aagtgctggg attacaagcg tgagccaccg tgcccggcca    720

acagttttta aatctgtgga gacttcattt cccttgatgc cttgcagccg cgccgactac    780

aactcccatc atgcctggca gccgctgggg ccgcgattcc gcacgtccct tacccgcttc    840

actagtcccg gcattcttcg ctgttttcct aactcgcccg cttgactagc gccctggaac    900

agccatttgg gtcgtggagt gcgagcacgg ccggccaatc gccgagtcag agggccagga    960

ggggcgcggc cattcgccgc ccggcccctg ctccgtggct ggttttctcc gcgggcgcct   1020

cgggcggaac ctggagataa tggcagcac ctgggggagc cctggctggg tgcggctcgc   1080

tctttgcctg acgggcttag tgctctcgct ctacgcgctg cacgtgaagg cggcgcgcgc   1140

ccgggaccgg gattaccgcg cgctctgcga cgtgggcacc gccatcagct gttcgcgcgt   1200

cttctcctcc aggtgtgcac gggagtggga ggcgtggggc ctcggagcag ggcggccagg   1260

atgccagatg attattctgg agtctgggat cggtgtgccc ggggaacgga cacggggctg   1320

gactgctcgc ggggtcgttg cacaggggct gagctaccca gcgatactgg tgttcgaaat   1380
```

-continued

```
aagagtgcga ggcaagggac cagacagtgc tggggactgg gattattccg gggactcgca   1440
cgtgaattgg atgccaagga ataacggtga ccaggaaagg cggggaggca ggatggcggt   1500
agagattgac gatggtctca aggacggcgc gcaggtgaag gggggtgttg gcgatggctg   1560
cgcccaggaa caaggtggcc cggtctggct gtgcgtgatg gccaggcgtt agcataatga   1620
cggaatacag aggaggcgag tgagtggcca gggagctgga gattctgggg tccagggcaa   1680
agataatctg cccccgactc ccagtctctg atgcaaaacc gagtgaaccg ttataccagc   1740
cttgccattt taagaattac ttaagggccg ggcgcggtgg cccactcctg taatcccagc   1800
actttgggag gccgaggcgg atggatcact tgaagtcagg agttgaccag cctggccaac   1860
atggtgaaag cctgtctcta ccaaaaatag aaaaattaat cgggcgctat ggcgggtgcc   1920
ttaatcccag ctactcgggg gggctaaggc aggagaatcg cttgaacccg ggaggcggag   1980
gtttcagtga gccgagatcg cgccactgca ctccagcctg ggccagagtg agactccgtc   2040
tcaaaaaaaa aaaaaaaaaa aaaaaaaaag agacttactt aaggtctaag atgaaaagca   2100
gggcctacgg agtagccacg tccgggcctg gtctggggag aggggaggat agggtcagtg   2160
acatggaatc ctgacgtggc caaaggtgcc cggtgccagg agatcatcga cccttggact   2220
aggatgggag gtcggggaac agaggatagc ccaggtggct tcttggaaat cacctttctc   2280
gggcagggtc caaggcactg ggttgacagt cctaacctgg ttccacccca ccccacccct   2340
ctgccaggtg gggcaggggt ttcgggctgg tggagcatgt gctgggacag gacagcatcc   2400
tcaatcaatc caacagcata ttcggttgca tcttctacac actacagcta ttgttaggtg   2460
agtggctccg ccccctccct gcccgccccg ccccgcccct catccccctt ggtcagctca   2520
gccccactcc atgcaatctt ggtgatccac acagctgaca gccagctagc tgctcatcac   2580
ggagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
caccttagcc tcccaagcag ctggaatcac aggcgtgcac cactatgccc agctaatttt   2880
tgtttttgtt tttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt cctttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccatggtcct   3300
ggctgacaca tggttcagac ttggccgatt tatttaagaa attttattgc tcagaacttt   3360
ccctccctgg gcaatggcaa gagcttcaga gaccagtccc ttggagggga cctgttgaag   3420
ccttcttttt tttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
```

-continued

```
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ctggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
tgtgagcctt gcctaagggg gcatatctgg gtccctagaa ggccctagat gtggggcttc   4740
tagattaccc cctcctcctg ccatacccgc acatgacaat ggaccaaatg tgccacacgc   4800
tcgctctttt ttacacccag tgcctctgac tctgtcccca tgggctggtc tccaaagctc   4860
tttccattgc ccagggaggg aaggttctga gcaataaagt ttcttagatc aatcagccaa   4920
gtctgaacca tgtgtctgcc atggactgtg gtgctgggcc tccctcggtg ttgccttctc   4980
tggagctggg aagggtgagt cagagggaga gtggagggcc tgctgggaag ggtggttatg   5040
ggtagtctca tctccagtgt gtggagtcag caaggcctgg ggcaccattg gcccccaccc   5100
ccaggaaaca ggctggcagc tcgctcctgc tgcccacagg agccaggcct cctctcctgg   5160
gaaggctgag cacacacctg gaagggcagg ctgcccttct ggttctgtaa atgcttgctg   5220
ggaagttctt ccttgagttt aactttaacc cctccagttg ccttatcgac cattccaagc   5280
cagtattggt agccttggag ggtcagggcc aggttgtgaa ggtttttgtt ttgcctatta   5340
tgccctgacc acttacctac atgccaagca ctgtttaaga acttgtgttg gcagggtgca   5400
gtggctcaca cctgtaatcc ctgtactttg ggaggccaag gcaggaggat cacttgaggc   5460
caggagttcc agaccagcct gggcaaaata gtgagacccc tgtctctaca aaaaaaaaaa   5520
aaaaaaaaaa ttagccaggc atggtggtgt atgtacctat agtcccaact aatcgggaag   5580
ctggcgggaa gactgcttga gcccagaagg ttgaggctgc agtgagccat gatcactgca   5640
ctccagcctg agcaacagag caagaccgtc tccaaaaaaa aacaaaaaac aaaaaaaaac   5700
ttgtgttaac gtgttaaact cgtttaatct ttacagtgat ttatgaggtg ggtactatta   5760
ttatccctat cttgatgata gggacagagt ggctaattag tatgcctgag atcacacagc   5820
tactgcagga ggctctcagg atttgaatcc acctggtcca tctggctcca gcatctatat   5880
gctttttttt ttgttggttt gtttttgaga cggac                              5915
```

<210> SEQ ID NO 16
<211> LENGTH: 5915
<212> TYPE: DNA
<213> ORGANISM: Homo sapiens

<400> SEQUENCE: 16

```
caccatcaga tgggacgtct gtgaaggaga gacctcatct ggcccacagc ttggaaagga     60
gagactgact gttgagttga tgcaagctca ggtgttgcca ggcgggcgcc atgatagtag    120
agaggttagg atactgtcaa gggtgtgtgt ggccaaagga gtggttctgt gaatgtatgg    180
gagaaaggga gaccgaccac caggaagcac tggtgaggca ggacccggga ggatgggagg    240
ctgcagcccg aatggtgcct gaaatagttt caggggaaat gcttggttcc cgaatcggat    300
cgccgtattc gctggatccc ctgatccgct ggtctctagg tcccggatgc tgcaattctt    360
acaacaggac ttggcatagg gtaagcgcaa atgctgttaa ccacactaac acactttttt    420
ttttcttttt tttttttgag acagagtctc actctgtcgg cctggctgga gtgcagtggc    480
acgatctcgg ctcactgcaa cctccggctc cccggctcaa gcaattctcc tgcctcagcc    540
tcccgagtag ctgggattac aggcatgtgc caccacgccc ggctaatttt tgtattttta    600
gttgagatgg ggtttcacca tgttggcgag gctggtcttg aactcctgac ctcaggtaat    660
ccgccagcct cggcctccca aagtgctggg attacaagcg tgagccaccg tgcccggcca    720
acagttttta aatctgtgga gacttcattt cccttgatgc cttgcagccg cgccgactac    780
aactcccatc atgcctggca gccgctgggg ccgcgattcc gcacgtccct tacccgcttc    840
actagtcccg gcattcttcg ctgttttcct aactcgcccg cttgactagc gccctggaac    900
agccatttgg gtcgtggagt gcgagcacgg ccggccaatc gccgagtcag agggccagga    960
ggggcgcggc cattcgccgc ccggcccctg ctccgtggct ggttttctcc gcgggcgcct   1020
cgggcggaac ctggagataa tgggcagcac ctgggggagc cctggctggg tgcggctcgc   1080
tctttgcctg acgggcttag tgctctcgct ctacgcgctg cacgtgaagg cggcgcgcgc   1140
ccgggaccgg gattaccgcg cgctctgcga cgtgggcacc gccatcagct gttcgcgcgt   1200
cttctcctcc aggtgtgcac gggagtggga ggcgtggggc ctcggagcag ggcggccagg   1260
atgccagatg attattctgg agtctgggat cggtgtgccc ggggaacgga cacggggctg   1320
gactgctcgc ggggtcgttg cacaggggct gagctaccca gcgatactgg tgttcgaaat   1380
aagagtgcga ggcaagggac cagacagtgc tggggactgg gattattccg gggactcgca   1440
cgtgaattgg atgccaagga ataacggtga ccaggaaagg cggggaggca ggatggcggt   1500
agagattgac gatggtctca aggacggcgc gcaggtgaag gggggtgttg gcgatggctg   1560
cgcccaggaa caaggtggcc cggtctggct gtgcgtgatg gccaggcgtt agcataatga   1620
cggaatacag aggaggcgag tgagtggcca gggagctgga gattctgggg tccagggcaa   1680
agataatctg cccccgactc ccagtctctg atgcaaaacc gagtgaaccg ttataccagc   1740
cttgccattt taagaattac ttaagggccg ggcgcggtgg cccactcctg taatcccagc   1800
actttgggag gccgaggcgg atggatcact tgaagtcagg agttgaccag cctggccaac   1860
atggtgaaag cctgtctcta ccaaaaatag aaaaattaat cgggcgctat ggcgggtgcc   1920
ttaatcccag ctactcgggg gggctaaggc aggagaatcg cttgaacccg ggaggcggag   1980
gtttcagtga gccgagatcg cgccactgca ctccagcctg ggccagagtg agactccgtc   2040
tcaaaaaaaa aaaaaaaaaa aaaaaaaaag agacttactt aaggtctaag atgaaaagca   2100
gggcctacgg agtagccacg tccgggcctg gtctggggag aggggaggat agggtcagtg   2160
acatggaatc ctgacgtggc caaaggtgcc cggtgccagg agatcatcga cccttggact   2220
aggatgggag gtcggggaac agaggatagc ccaggtggct tcttggaaat cacctttctc   2280
```

-continued

```
gggcagggtc caaggcactg ggttgacagt cctaacctgg ttccacccca ccccacccct   2340
ctgccaggtg gggcaggggt ttcgggctgg tggagcatgt gctgggacag gacagcatcc   2400
tcaatcaatc caacagcata ttcggttgca tcttctacac actacagcta ttgttaggtg   2460
agtggctccg ccccctccct gcccgccccg ccccgcccct catccccctt ggtcagctca   2520
gccccactcc atgcaatctt ggtgatccac acagctgaca gccagctagc tgctcatcac   2580
ggagcgtcct gcgggtgggg atgtggggag gtaactaaca ggagtctttt aattggttta   2640
agtactgtta gaggctgaag ggcccttaaa gacatcctag gtccccaggt tttttgtttg   2700
ttgttgtttt gagacagggt ctggctctgt tgcccaaagt gaggtctagg atgcccttag   2760
tgtgcactgg cgtgatctca gttcatggca acctctgcct ccctgcccaa gggatcctcc   2820
caccttagcc tcccaagcag ctggaatcac aggcgtgcac cactatgccc agctaatttt   2880
tgtttttgtt tttttttggt agagatggtg tctcgccatg ttgcccaggc tggtctcaag   2940
caatctgtct gcctcagcct cccaaagtgc tggggggatt acaggcgtga gctaccatgc   3000
cccaccaaca ccccagtttt gtggaaaaga tgccgaaatt cctttttaag gagaagctga   3060
gcatgagcta tcttttgtct catttagtgc tcagcaggaa aatttgtatc tagtcccata   3120
agaacagaga gaggaaccaa gggagtggaa gacgatggcg ccccaggcct tgctgatgcc   3180
atatgccgga gatgagacta tccattacca cccttcccag caggctccca cgctcccttt   3240
gagtcaccct tcccagctcc agagaaggca tcactgaggg aggcccagca ccatggtcct   3300
ggctgacaca tggttcagac ttggccgatt tatttaagaa attttattgc tcagaacttt   3360
ccctccctgg gcaatggcaa gagcttcaga gaccagtccc ttggaggggga cctgttgaag   3420
ccttcttttt tttttttttt aagaaataat cttgctctgt tgcccaggct ggagtgcagt   3480
ggcacaatca tagctcactg taacctggct caagcgatcc tcctgagtag ctaggactat   3540
aggcatgtca ctgcacccag ctaatttttt tttttttttt tttttttttt ttgcgacata   3600
gtctcgctct gtcaccaggc tggagtgcag tggcacgatc ttggctcact gcaacctctg   3660
cctcccgggt tcaagcaatt ttcctgcctc agcctcctga gtagctggga ctacaggcgc   3720
gtgtcaccac gcccagctaa tttttgtatt tttagtggag acagggtttc accatgttgg   3780
ctaggatggt ctcaatctct tgacctggtg atccatccgc cttggcctcc caaagtgcta   3840
ggattacagg cgtgagtcaa cctcaccggg cattttttttt ttgagacgaa gtcttgctct   3900
tgctgcccaa gctggaatgt ggtggcatga tctcggctca ctgcaacctc cacctcctag   3960
gttcaagcga ttctccacct tagcctcccc agcagctggg attacaggtg cccatcaaca   4020
cacccggcta atttttgtat ttttattaga gatggggttt tgccatgttg gccaggctgc   4080
tctcgaactc ctaacctcag gtgatccacc cccattggcc tcccaaaata ctgggattac   4140
aggcatgagc caccgtgccc agctgaattt ctaaattttt gatagagatc gggtctttct   4200
atgttgccca agctggtctt gaactcctag cctaaagcag tcttcccacc tcggcctccc   4260
agagtgtttg gaatacgtgc gtaagccacc acatctgccc tggagcctct tgttttagag   4320
acccttccca gcagctcctg gcatctaggt agtgcagtga catcatggag tgttcgggag   4380
gtggccagtg cctgaagccc acaccggacc ctcttctgcc ttgcaggttg cctgcggaca   4440
cgctgggcct ctgtcctgat gctgctgagc tccctggtgt ctctcgctgg ttctgtctac   4500
ttggcctgga tcctgttctt cgtgctctat gatttctgca ttgtttgtat caccacctat   4560
gctatcaacg tgagcctgat gtggctcagt ttccggaagg tccaagaacc ccagggcaag   4620
gctaagaggc actgagccct caacccaagc caggctgacc tcatctgctt tgctttggca   4680
```

-continued

```
tgtgagcctt gcctaagggg gcatatctgg gtccctagaa ggccctagat gtggggcttc   4740

tagattaccc cctcctcctg ccatacccgc acatgacaat ggaccaaatg tgccacacgc   4800

tcgctctttt ttacacccag tgcctctgac tctgtcccca tgggctggtc tccaaagctc   4860

tttccattgc ccagggaggg aaggttctga gcaataaagt ttcttagatc aatcagccaa   4920

gtctgaacca tgtgtctgcc atggactgtg gtgctgggcc tccctcggtg ttgccttctc   4980

tggagctggg aagggtgagt cagagggaga gtggagggcc tgctgggaag ggtggttatg   5040

ggtagtctca tctccagtgt gtggagtcag caaggcctgg ggcaccattg gcccccaccc   5100

ccaggaaaca ggctggcagc tcgctcctgc tgcccacagg agccaggcct cctctcctgg   5160

gaaggctgag cacacacctg gaagggcagg ctgcccttct ggttctgtaa atgcttgctg   5220

ggaagttctt ccttgagttt aactttaacc cctccagttg ccttatcgac cattccaagc   5280

cagtattggt agccttggag ggtcagggcc aggttgtgaa ggtttttgtt ttgcctatta   5340

tgccctgacc acttacctac atgccaagca ctgtttaaga acttgtgttg gcagggtgca   5400

gtggctcaca cctgtaatcc ctgtactttg ggaggccaag gcaggaggat cacttgaggc   5460

caggagttcc agaccagcct gggcaaaata gtgagacccc tgtctctaca aaaaaaaaaa   5520

aaaaaaaaaa ttagccaggc atggtggtgt atgtacctat agtcccaact aatcgggaag   5580

ctggcgggaa gactgcttga gcccagaagg ttgaggctgc agtgagccat gatcactgca   5640

ctccagcctg agcaacagag caagaccgtc tccaaaaaaa aacaaaaaac aaaaaaaaac   5700

ttgtgttaac gtgttaaact cgtttaatct ttacagtgat ttatgaggtg ggtactatta   5760

ttatccctat cttgatgata gggacagagt ggctaattag tatgcctgag atcacacagc   5820

tactgcagga ggctctcagg atttgaatcc acctggtcca tctggctcca gcatctatat   5880

gctttttttt ttgttggttt gtttttgaga cggac                              5915
```

<210> SEQ ID NO 17
<211> LENGTH: 15
<212> TYPE: DNA
<213> ORGANISM: Artificial
<220> FEATURE:
<223> OTHER INFORMATION: vk2581 G>C VIC probe sequence

<400> SEQUENCE: 17

```
tcatcacgga gcgtc                                                      15
```

<210> SEQ ID NO 18
<211> LENGTH: 15
<212> TYPE: DNA
<213> ORGANISM: Artificial
<220> FEATURE:
<223> OTHER INFORMATION: vk2581 G>C FAM probe sequence

<400> SEQUENCE: 18

```
tcatcaccga gcgtc                                                      15
```

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19

```
ggtgatccac acagctgaca                                                 20
```

<210> SEQ ID NO 20
<211> LENGTH: 23
<212> TYPE: DNA
<213> ORGANISM: Artificial
<220> FEATURE:
<223> OTHER INFORMATION: PCR primer

<400> SEQUENCE: 20
cctgttagtt acctccccac atc 23

<210> SEQ ID NO 21
<211> LENGTH: 15
<212> TYPE: DNA
<213> ORGANISM: Artificial
<220> FEATURE:
<223> OTHER INFORMATION: vk3294 T>C VIC probe sequence

<400> SEQUENCE: 21
ccaggaccat ggtgc 15

<210> SEQ ID NO 22
<211> LENGTH: 15
<212> TYPE: DNA
<213> ORGANISM: Artificial
<220> FEATURE:
<223> OTHER INFORMATION: vk3294 T>C FAM probe sequence

<400> SEQUENCE: 22
ccaggaccgt ggtgc 15

<210> SEQ ID NO 23
<211> LENGTH: 20
<212> TYPE: DNA
<213> ORGANISM: Artificial
<220> FEATURE:
<223> OTHER INFORMATION: PCR primer

<400> SEQUENCE: 23
gctccagaga aggcatcact 20

<210> SEQ ID NO 24
<211> LENGTH: 22
<212> TYPE: DNA
<213> ORGANISM: Artificial
<220> FEATURE:
<223> OTHER INFORMATION: PCR primer

<400> SEQUENCE: 24
gccaagtctg aaccatgtgt ca 22

<210> SEQ ID NO 25
<211> LENGTH: 15
<212> TYPE: DNA
<213> ORGANISM: Artificial
<220> FEATURE:
<223> OTHER INFORMATION: vk4769 G>A VIC probe sequence

<400> SEQUENCE: 25
atacccgcac atgac 15

<210> SEQ ID NO 26
<211> LENGTH: 16
<212> TYPE: DNA
<213> ORGANISM: Artificial
<220> FEATURE:
<223> OTHER INFORMATION: vk4769 G>A FAM probe sequence

<400> SEQUENCE: 26 cataccaca catgac 16

<210> SEQ ID NO 27
<211> LENGTH: 22
<212> TYPE: DNA
<213> ORGANISM: Artificial
<220> FEATURE:
<223> OTHER INFORMATION: PCR primer

<400> SEQUENCE: 27
gtccctagaa ggccctagat gt 22

<210> SEQ ID NO 28
<211> LENGTH: 21
<212> TYPE: DNA
<213> ORGANISM: Artificial
<220> FEATURE:
<223> OTHER INFORMATION: PCR primer

<400> SEQUENCE: 28
gtgtggcaca tttggtccat t 21

<210> SEQ ID NO 29
<211> LENGTH: 19
<212> TYPE: DNA
<213> ORGANISM: Artificial
<220> FEATURE:
<223> OTHER INFORMATION: PCR primer

<400> SEQUENCE: 29
ccaatcgccg agtcagagg 19

<210> SEQ ID NO 30
<211> LENGTH: 20
<212> TYPE: DNA
<213> ORGANISM: Artificial
<220> FEATURE:
<223> OTHER INFORMATION: PCR primer

<400> SEQUENCE: 30
cccagtcccc agcactgtct 20

<210> SEQ ID NO 31
<211> LENGTH: 20
<212> TYPE: DNA
<213> ORGANISM: Artificial
<220> FEATURE:
<223> OTHER INFORMATION: PCR primer

<400> SEQUENCE: 31
aggggaggat agggtcagtg 20

<210> SEQ ID NO 32
<211> LENGTH: 21
<212> TYPE: DNA
<213> ORGANISM: Artificial
<220> FEATURE:
<223> OTHER INFORMATION: PCR primer

<400> SEQUENCE: 32
cctgttagtt acctccccac a 21

<210> SEQ ID NO 33

-continued

```
<211> LENGTH: 20
<212> TYPE: DNA
<213> ORGANISM: Artificial
<220> FEATURE:
<223> OTHER INFORMATION: PCR primer

<400> SEQUENCE: 33

atacgtgcgt aagccaccac                                                20


<210> SEQ ID NO 34
<211> LENGTH: 20
<212> TYPE: DNA
<213> ORGANISM: Artificial
<220> FEATURE:
<223> OTHER INFORMATION: PCR primer

<400> SEQUENCE: 34

acccagatat gcccccttag                                                20
```